United States Patent
Manoharan et al.

(10) Patent No.: US 6,600,032 B1
(45) Date of Patent: *Jul. 29, 2003

(54) 2'-O-AMINOETHYLOXYETHYL-MODIFIED OLIGONUCLEOTIDES

(75) Inventors: Muthiah Manoharan, Carlsbad; Phillip Dan Cook, Fallbrook, both of CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/370,625

(22) Filed: Aug. 6, 1999

Related U.S. Application Data

(63) Continuation-in-part of application No. 09/130,566, filed on Aug. 7, 1998, now Pat. No. 6,043,352.

(51) Int. Cl.$^7$ ............................................. C07H 21/04
(52) U.S. Cl. .......................................... 536/26.6; 435/6
(58) Field of Search ............................... 435/6; 536/26.6

(56) References Cited

U.S. PATENT DOCUMENTS

| | | |
|---|---|---|
| 3,687,808 A | 8/1972 | Merigan et al. ........... 195/28 N |
| 4,469,863 A | 9/1984 | Ts'o et al. ..................... 536/27 |
| 4,725,677 A | 2/1988 | Köster et al. ................. 536/27 |
| 5,034,506 A | 7/1991 | Summerton et al. ........ 528/391 |
| 5,124,047 A | 6/1992 | Quach et al. ................ 210/699 |
| 5,138,045 A | 8/1992 | Cook et al. .................... 536/27 |
| RE34,069 E | 9/1992 | Köster et al. ................. 536/27 |
| 5,212,295 A | 5/1993 | Cook ........................ 536/26.7 |
| 5,214,134 A | 5/1993 | Weis et al. ................. 536/25.3 |
| 5,218,105 A | 6/1993 | Cook et al. ............... 536/25.31 |
| 5,223,618 A | 6/1993 | Cook et al. ................. 544/276 |
| 5,278,302 A | 1/1994 | Caruthers et al. .......... 536/24.5 |
| 5,321,131 A | 6/1994 | Agrawal et al. ......... 536/25.34 |
| 5,359,044 A | 10/1994 | Cook et al. ................ 536/23.1 |
| 5,378,825 A | 1/1995 | Cook et al. .............. 536/25.34 |
| 5,386,023 A | 1/1995 | Sanghvi et al. ............ 536/25.3 |
| 5,434,257 A | 7/1995 | Matteucci et al. ......... 536/24.3 |
| 5,455,233 A | 10/1995 | Spielvogel et al. ............ 514/44 |
| 5,457,191 A | 10/1995 | Cook et al. .............. 536/27.13 |
| 5,459,255 A | 10/1995 | Cook et al. .............. 536/27.13 |
| 5,466,677 A | 11/1995 | Baxter et al. .................. 514/44 |
| 5,470,967 A | 11/1995 | Huie et al. ................. 536/24.3 |
| 5,489,677 A | 2/1996 | Sanghvi et al. ............ 536/22.1 |
| 5,506,351 A | 4/1996 | McGee ...................... 536/55.3 |
| 5,519,126 A | 5/1996 | Hecht ........................ 536/24.3 |
| 5,541,307 A | 7/1996 | Cook et al. ................ 536/23.1 |
| 5,543,507 A | 8/1996 | Cook et al. ................ 536/23.1 |
| 5,571,902 A | 11/1996 | Ravikumar et al. ........ 536/22.1 |
| 5,578,718 A | 11/1996 | Cook et al. .............. 536/27.21 |
| 5,587,361 A | 12/1996 | Cook et al. ................... 514/44 |
| 5,587,469 A | 12/1996 | Cook et al. ................ 536/23.1 |
| 5,817,781 A | 10/1998 | Swaminathan et al. | |

FOREIGN PATENT DOCUMENTS

| | | |
|---|---|---|
| EP | 0 216 860 B1 | 10/1992 |
| WO | WO 89/12060 | 12/1989 |
| WO | WO 90/15065 | 12/1990 |
| WO | WO 91/08213 | 6/1991 |
| WO | WO 91/10671 | 7/1991 |
| WO | WO 91/15500 | 10/1991 |
| WO | WO 91/18997 | 12/1991 |
| WO | WO 92/02258 | 2/1992 |
| WO | WO 92/03568 | 3/1992 |
| WO | WO 92/05186 | 4/1992 |
| WO | WO 92/19637 | 11/1992 |
| WO | WO 92/20822 | 11/1992 |
| WO | WO 92/20823 | 11/1992 |
| WO | WO 93/13121 | 7/1993 |
| WO | WO 94/02501 | 2/1994 |
| WO | WO 97/46569 | 12/1997 |

OTHER PUBLICATIONS

Abe, et al., "Conformational Energies and the Random–Coil Dimensions and Dipole Moments of the Polyoxides $CH_3O[(CH_2)_yO]_xCH_3$", J. Am. Chem. Soc., 1976, 98, 6468–6476.

Altmann, et al., "Second Generation of Antisense Oligonucleotides: From Nuclease Resistance to Biological Efficacy in Animals", Chimia, 1996, 50, 168–176.

Altmann, et al., "Second-generation antisense oligonucleotides: structure–activity relationships and the design of improved signal–transduction inhibitors", Biochem. Soc. Trans., 1996, 24, 630–637.

Altmann, et al., "Second Generation Antisense Oligonucleotides—Inhibition of PKCα and c–RAF Kinase Expression by Chimeric Oligonucleotides Incorporating 6'–Substituted Carbocyclic Nucleosides and 2'–O–Ethylene Glycol Substituted Ribonucleosides", Nucleosides & Nucleotides, 1997, 16, 917–926.

Anderson, et al., Meeting Abstracts, International Hepatitis Meeting, Hawaii, 1997.

Baker, B.F. et al., "2'–O–(2–Methoxy)ethyl–modified Anti–intercellular Adhesion Molecule 1 (ICAM–1) Oligonucleotides Selectively Increase the ICAM–1 Translation Initiation Complex in Human Umbilical Vein Endothelial Cells", J. Biol. Chem., 1997, 272, 11994–12000.

Beal et al., "Second Structural Motif for Recognition of DNA by Oligonucleotide–Directed Triple–Helix Formation", Science, 1991, 251, 1360–1363.

(List continued on next page.)

Primary Examiner—Jezia Riley
(74) Attorney, Agent, or Firm—Woodcock Washburn LLP

(57) ABSTRACT

2'-O-Modified ribosyl nucleosides and modified oligomeric compounds containing such nucleosidic monomers are disclosed. Oligomeric compounds are disclosed that have increased binding affinity as shown by molecular modeling experiments. The 2'-O-modified nucleosides of the invention include ring structures that position the sugar moiety of the nucleosides preferentially in 3' endo geometries.

31 Claims, No Drawings

OTHER PUBLICATIONS

Beaucage, S.L. et al., "Advances in the Synthesis of Oligonucleotides by the Phosphoramidite Approach", *Tetrahedron*, 1992, 48, 2223–2311.

Beese, et al., "Structural basis for the 3'–5' exonuclease activity of *Escherichia coli* DNA polymerase I: a two metal ion mechanism", *EMBO J.*, 1991, 10, 25–33.

Bock et al., "Selection of single–stranded DNA molecules that bind and inhibit human thrombin", *Nature*, 1992, 355, 564–566.

Brautigam, et al., "Structural Principles for the Inhibition of the 3'–5' Exonuclease Activity of *Escherichia coli* DNA Polymerase I by Phosphorothioates", *J. Mol. Biol.*, 1998, 277, 363–377.

Conte, et al., "Conformational properties and thermodynamics of the RNA duplex r(CGCAAAUUUGCG)$_2$: comparison with the DNA analogue d(CGCAAATTTGCG)$_2$", *Nucleic Acids Res.*, 1997, 25, 2627–2634.

Cowsert, L.M., "In vitro and in vivo activity of antisense inhibitors of ras: potential for clinical development", *Anti–cancer Drug Design*, 1997, 12, 359–371.

Crooke et al., "Progress in Antisense Therapeutics", *Med. Res. Rev.*, 1996, 16, 319–344.

Crooke, S.T. et al., "Pharmacokinetic Properties of Several Novel Oligonucleotide Analogs in mice", *J. Pharmacol. Exp. Therapeutics*, 1996, 277, 923–937.

De Mesmacker, A. et al., "Antisense Oligonucleotides", *Acc. Chem. Res.*, 1995, 28, 366–374.

Egli et al., "RNA Hydration: A Detailed Look", *Biochemistry*, 1996, 35, 8489–8494.

Englisch, U. et al., "Chemically Modified Oligonucleotides as Probes and Inhibitors", *Angew. Chem. Int. Ed. Eng.*, 1991, 30, 613–629.

Federoff, et al., "Structure of a DNA: RNA Hybrid Duplex Why Rnase H Does Not Cleave Pure RNA", *J. Mol. Biol.*, 1993, 233, 509–523.

Freier, S.M. et al., "The ups and downs of nucleic acid duplex stability: structure–stability studies on chemically–modified DNA:RNA duplexes", *Nucl. Acids Res.*, 1997, 25, 4429–4443.

Gonzalez, et al., "Structure and Dynamics of a DNA–RNA Hybrid Duplex with a Chiral Phosphorothioate Moiety: NMR and Molecular Dynamics with Conventional and Time Averaged Restraints", *Biochemistry*, 1995, 34, 4969–4982.

Griffin et al., "In Vivo Anticoagulant Properties of a Novel Nucleotide–Based Thrombin Inhibitor and Demonstration of Regional Anticoagulation in Extracorporeal Circuits", *Blood*, 1993, 81, 3271–3276.

Hanecak, et al., "Antisense Oligonucleotide Inhibition of Hepatitis C VirusGene Expression in Transformed Hepatocytes", *J. Virol.*, 1996, 70, 5203–5212.

Horton et al., "The Structure of an RNA/DNA Hybrid: A Substrate of the Ribonuclease Activity of HIV–1 Reverse Transcriptase", *J. Mol. Biol.*, 1996, 264, 521–533.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kroschwitz, J.I., "Polynucleotides", *Concise Encyclopedia of Polymer Science and Engineering*, 1990, John Wiley & Sons, New York, 858–859.

Lane, et al., "NMR assignment and solution conformation of the DNA–RNA hybrid duplex d(GTGAACTT).r(AAGUU-CAC)", *Eur. J. Biochem.*, 1993, 215, 297–306.

Lesnik, et al., "Relative Thermodynamic Stability of DNA, RNA, and DNA: RNA Hybrid Duplexes: Relationship with Base Composition and Structure", *Biochemistry*, 1995, 34, 10807–10815.

Lesnik, E.A. et al., "Oligodeoxynucleotides Containing 2'–O–Modified Adenosine Synthesis and Effects of Stability of DNA:RNA Duplexes", *Biochem.*, 1993, 32, 7832–7838.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Manoharan M. et al., "Cholic Acid–Oligonucliotide Conjugates for Antisense Applications", *Bioorganic Med. Chem. Letts.*, 1994, 4, 1053–1060.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan, M. et al., "Lipidic Nucleic Acids", *Tetrahedron Letts.*, 1995, 36, 3651–3654.

Manoharan M. et al., "Oligonucleotide Conjugates: Alteration of the Pharmacokinetic Properties of Antisense Agents", *Nucleosides and Nucleotides*, 1995, 14, 969–973.

Martin, P., "Ein neuer Zugang zu 2'–O–Alkylribonucleosiden und Eigenschaften deren Oligonucleotide", *Helvetica Chemica Acta*, 1995, 78, 486–504.

Miller, P.S. et al., "A New approach to chemotherapy based on molecular biology and nucleic acid chemistry: Matagen (masking tape for gene expression)", *Anti–Cancer Drug Des.*, 1987, 2, 117–128.

Milligan, "Current Concepts in Antisense Drug Design", *J. Med. Chem.*, 1993, 36, 1923–1937.

Mishra, R.K. et al., "Improved leishmanicidal effect of phosphorotioate antisense oligonucleotides by LDL–medicated delivery", *Biochim. et Biophysica*, 1995, 1264, 229–237.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Searle, et al., "On the stability of nucleic acid structures in solution: enthalpy–entropy compensations, internal rotations and reversibility", *Nucleic Acids Res.*, 1993, 21, 2051–2056.

Shea, R.G. et al., "Synthesis, hybridization properties and antiviral activity of lipid–oligodeoxynucletide conjugates", *Nucl. Acids Res.*, 1990, 18, 3777–3783.

Svinarchuk, F.P. et al., "Inhibition of HIV proliferation in MT–4 cells by antisense oligonucleotide conjugated to lipophilic groups", *Biochimie*, 1993, 79, 49–54.

Stein, C.A. et al., "Oligodeoxynucleotides as Inhibitors of Gene Expression: A Review", *Cancer Res.*, 1988, 48, 2659–2668.

Uhlmann, E. et al., "Antisense Oligonucleotides: A New Therapeutic Principle", *Chem. Reviews*, 1990, 90, 544–584.

Wagner, et al., "Antisense Gene Inhibition by Oligonucleotides Containing C–5 Propyne Pyrimidines", *Science*, 1993, 260, 1510–1513.

Wolfe, et al., "The Gauche Effect. Some Stereochemical Consequences of Adjacent Electron Pairs and Polar Bonds", *Acc. Chem. Res.*, 1972, 5, 102–111.

Young, et al., "Triple helix formation inhibits transcription elongation in vitro", *Proc. Natl. Acad. Sci.*, 1991, 88, 10023–10026.

Agrawal et al. (eds.), "Methods of Molecular Biology", in *Protocols for Oligonucleotide Conjugates*, Agrawal, S. (ed.) Humana Press, New Jersey, 1994, vol. 26, 1–72.

Atherton, E. et al., "The Fluorenylmethoxycarbonyl Amino Protecting Group", in *The Peptides*, Udenfried, S. et al. (eds.), Academic Press, 1987, 9, 1–39.

Beaucage, S.L. et al., "The Functionalization of Oligonucleotides Via Phosphoramidite Derivatives," *Tetrahedron*, 1993, 49(10), 1925–1963.

Beaucage, S.L. et al., "The Synthesis of Specific Ribonucleotides and Unrelated Phosphorylated Biomolecules by the Phosphoramidite Method," *Tetrahedron*, 1993, 49(46), 10441–10488.

Coull, J.M. et al., "Synthesis and Characterization of a Carbamate–Linked Oligonucleotide", *Tetrahedron Letts.*, 1987, 28, 745–748.

Hewitt, J.M. et al., "Structural Determination of Silicon Containing Oligonucleotides by $^1H$–$^{29}Si$ Long–Range Heteronuclear Multiple Quantum Correlation NMR Spectroscopy", 1992, 11, 1661–1666.

Manoharan, M. et al., "Chemical Modifications to Improve Uptake and Bioavailability of Antisense Oligonucleotides", *Annals NY Acad. Sciences*, 1992, 660, 306–309.

Mertes, M.P. et al., "Synthesis of Carbonate Analogs of Dinucleosides. 3'-Thymidinyl 5'-Thymidinyl Carbonate, 3'-Thymidinyl 5'-(5-Fluoro-2'-deoxyuridinyl) Carbonate, and 3'-(5-Fluoro-2'-deoxyuridinyl) 5'-Thymidinyl Carbonate", *J. Med. Chem.*, 1969, 12, 154–157.

Mungall, W.S. et al., "Carbamate Analogues of Oligonucleotides", *J. Org. Chem.*, 1977, 42, 703–706.

Musicki, B. et al., "Synthesis of Carbohydrate Sulfonates and Sulfonate Esters", *J. Org. Chem.*, 1990, 55, 4231–4233.

Reynolds, R.C. et al., "Synthesis of Thymidine Dimers Containing Internucleoside Sulfonate and Sulfonamide Linkages", *J. Org. Chem.*, 1992, 57, 2983–2985.

Samukov, V.V. et al., "2-(4-Nitrophenyl) sulfonylethoxycarbonyl (Nse) Group as a Base–Labile α–Amino Protection for Solic Phase Peptide Synthesis", *Tetra. Letts.*, 1994, 35, 7821–7824.

Sood, A. et al., "Boron–Containing Nucleic Acids. 2. Synthesis of Oligodeoxynucleoside Boranophosphates", *J. Am. Chem. Soc.*, 1990, 112, 9000–9001.

Stirchak, E.P. et al., "Uncharged stereoregular nucleic acid analogs: 2. Morpholino nucleoside oligomer with carbamate internucleoside linkages", *Nucl. Acids Res.*, 1989, 17, 6129–6134.

Stirchak, E.P. et al., "Uncharged Stereoregular Nucleic Acid Analogs. I. Synthesis of a Cytosine–Containing Oligomer with Carbamate Internucleoside Linkages", *J. Org Chem.*, 1987, 52, 4202–4206.

Vasseur, J.J. et al., "Oligonucleosides: Synthesis of a Novel Methylhydroxylamine–linked Nucleoside Dimer and Its Incorporation into Antisense Sequences", *J. Am. Chem. Soc.*, 1992, 114, 4006–4007.

Verhart, C.G.J., "New base–labile amino–protective groups for peptide synthesis", *Recl. Trav. Chim. Pays–Bas*, 1988, 107, 621–626.

Wang, H. et al., "Solid Phase Synthesis of Neutral Oligonucleotide Analogues", *Tetrahedron Letts.*, 1991, 32, 7385–7388.

2'-O-AMINOETHYLOXYETHYL-MODIFIED OLIGONUCLEOTIDES

RELATED APPLICATION DATA

This patent application is a continuation-in-part of application Ser. No. 09/130,566, filed Aug. 7, 1998, now U.S. Pat. No. 6,043,352 the contents of which are incorporated herein by reference.

FIELD OF THE INVENTION

The present invention relates to nucleosidic monomers and oligomeric compounds incorporating such nucleosidic monomers, and methods of using such oligomeric compounds. The oligomeric compounds of the invention are useful for therapeutic and investigative purposes. More specifically, the present invention is directed to the use of oligomeric compounds having 2'-O-modifications that will increase their affinity and nuclease resistance.

BACKGROUND OF THE INVENTION

It is well known that most of the bodily states in mammals, including most disease states, are affected by proteins. Classical therapeutic modes have generally focused on interactions with such proteins in an effort to moderate their disease-causing or disease-potentiating functions. Recently, however, attempts have been made to moderate the actual production of such proteins by interactions with molecules that direct their synthesis, such as intracellular RNA. By interfering with the production of proteins, maximum therapeutic effect and minimal side effects may be realized. It is the general object of such therapeutic approaches to interfere with or otherwise modulate gene expression leading to undesired protein formation.

One method for inhibiting specific gene expression is the use of oligonucleotides. Oligonucleotides are now accepted as therapeutic agents with great promise, and are known to hybridize to single-stranded DNA or RNA molecules. Hybridization is the sequence-specific base pair hydrogen bonding of nucleobases of the oligonucleotide to the nucleobases of the target DNA or RNA molecule. Such nucleobase pairs are said to be complementary to one another. The concept of inhibiting gene expression through the use of sequence-specific binding of oligonucleotides to target RNA sequences, also known as antisense inhibition, has been demonstrated in a variety of systems, including living cells (see, e.g., Wagner et al., Science (1993) 260:1510–1513; Milligan et al., J. Med. Chem., (1993) 36:1923–37; Uhlmann et al., Chem. Reviews, (1990) 90:543–584; Stein et al., Cancer Res., (1988) 48:2659–2668).

The events that provide the disruption of the nucleic acid function by antisense oligonucleotides (Cohen in Oligonucleotides: *Antisense Inhibitors of Gene Expression,* (1989) CRC Press, Inc., Boca Raton, Fla.) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides: Miller, P. S. and Ts'O, P.O.P. (1987) *Anti-Cancer Drug Design,* 2:117–128, and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Oligonucleotides may also bind to duplex nucleic acids to form triplex complexes in a sequence specific manner via Hoogsteen base pairing (Beal et al., Science, (1991) 251:1360–1363; Young et al., Proc. Natl. Acad. Sci. (1991) 88:10023–10026). Both antisense and triple helix therapeutic strategies are directed towards nucleic acid sequences that are involved in or responsible for establishing or maintaining disease conditions. Such target nucleic acid sequences may be found in the genomes of pathogenic organisms including bacteria, yeasts, fungi, protozoa, parasites, viruses, or may be endogenous in nature. By hybridizing to and modifying the expression of a gene important for the establishment, maintenance or elimination of a disease condition, the corresponding condition may be cured, prevented or ameliorated.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides may also be of therapeutic value when they bind to non-nucleic acid biomolecules such as intracellular or extracellular polypeptides, proteins, or enzymes. Such oligonucleotides are often referred to as "aptamers" and they typically bind to and interfere with the function of protein targets (Griffin, et al., Blood, (1993), 81:3271–3276; Bock, et al., Nature, (1992) 355: 564–566).

Oligonucleotides and their analogs (oligomeric compounds) have been developed and used for diagnostic purposes, therapeutic applications and as research reagents. For use as therapeutics, oligonucleotides preferably are transported across cell membranes or be taken up by cells, and appropriately hybridize to target DNA or RNA. These functions are believed to depend on the initial stability of the oligonucleotides toward nuclease degradation. A deficiency of unmodified oligonucleotides which affects their hybridization potential with target DNA or RNA for therapeutic purposes is their degradation by a variety of ubiquitous intracellular and extracellular nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and resist nuclease degradation. Modifications have been made, for example, to the phosphate backbone to increase the resistance to nucleases. These modifications include use of linkages such as methyl phosphonates, phosphorothioates and phosphorodithioates, and the use of modified sugar moieties such as 2'-O-alkyl ribose. Other oligonucleotide modifications include those made to modulate uptake and cellular distribution. A number of modifications that dramatically alter the nature of the internucleotide linkage have also been reported in the literature. These include non-phosphorus linkages, peptide nucleic acids (PNA's) and 2'-5' linkages. Another modification to oligonucleotides, usually for diagnostic and research applications, is labeling with non-isotopic labels, e.g., fluorescein, biotin, digoxigenin, alkaline phosphatase, or other reporter molecules.

Over the last ten years, a variety of synthetic modifications have been proposed to increase nuclease resistance, or to enhance the affinity of the antisense strand for its target mRNA (Crooke et al., *Med. Res. Rev.*, 1996, 16, 319–344; De Mesmaeker et al., *Acc. Chem. Res.*, 1995, 28, 366–374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807–10815; Conte et al., *Nucleic Acids Res.*, 1997, 25, 2627–2634). The increased stability of RNA has been attributed to several structural features, most notably the improved base stacking interactions that result from an A-form geometry (Searle et al., *Nucleic Acids Res.*, 1993, 21, 2051–2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489–8494).

DNA:RNA hybrid duplexes, however, are usually less stable than pure RNA:RNA duplexes and, depending on their sequence, may be either more or less stable than DNA:DNA duplexes (Searle et al., *Nucleic Acids Res.*, 1993, 21, 2051–2056). The structure of a hybrid duplex is intermediate between A- and B-form geometries, which may result in poor stacking interactions (Lane et al., *Eur. J. Biochem.*, 1993, 215, 297–306; Fedoroff et al., *J. Mol. Biol.*, 1993, 233, 509–523; Gonzalez et al., *Biochemistry*, 1995, 34, 4969–4982; Horton et al., *J. Mol. Biol.*, 1996, 264, 521–533). The stability of a DNA:RNA hybrid a significant aspect of antisense therapies, as the proposed mechanism requires the binding of a modified DNA strand to a mRNA strand. Ideally, the antisense DNA should have a very high binding affinity with the mRNA. Otherwise, the desired interaction between the DNA and target mRNA strand will occur infrequently, thereby decreasing the efficacy of the antisense. oligonucleotide.

One synthetic 2'-modification that imparts increased nuclease resistance and a very high binding affinity to nucleotides is the 2'-methoxyethoxy (MOE, 2'-OCH$_2$CH$_2$OCH$_3$) side chain (Baker et al., *J. Biol. Chem.*, 1997, 272, 11944–12000; Freier et al., *Nucleic Acids Res.*, 1997, 25, 4429–4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429–4443). 2'-O-Methoxyethyl-substituted also have been shown to be antisense inhibitors of gene expression with promising features for in vivo use (Martin, P., *Helv. Chim. Acta*, 1995, 78, 486–504; Altmann et al., *Chimia*, 1996, 50, 168–176; Altmann et al., *Biochem. Soc. Trans.*, 1996, 24, 630–637; and Altmann et al., *Nucleosides Nucleotides*, 1997, 16, 917–926). Relative to DNA, they display improved RNA affinity and higher nuclease resistance. Chimeric oligonucleotides with 2'-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

Although the known modifications to oligonucleotides, including the use of the 2'-O-methoxyethyl modification, have contributed to the development of oligonucleotides for various uses, there still exists a need in the art for further modifications that will impart enhanced hybrid binding affinity and/or increased nuclease resistance to oligonucleotides and their analogs.

SUMMARY OF THE INVENTION

The present invention provides oligomeric compounds having at least one 2'—O—CH$_2$CH$_2$—O—CH$_2$CH$_2$—N(R$_1$)(R$_2$) modified nucleoside. Preferred oligomeric compounds of the invention are those that include at least one nucleoside of the formula:

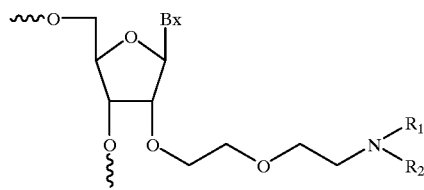

wherein
  Bx is a heterocyclic base;
  each R$_1$ and R$_2$ is, independently, H, a nitrogen protecting group, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, wherein said substitution is OR$_3$, SR$_3$, NH$_3^+$, N(R$_3$)(R$_4$), guanidino or acyl where said acyl is an acid, amide or an ester;
  or R$_1$ and R$_2$, together, are a nitrogen protecting group or are joined in a ring structure that optionally includes an additional heteroatom selected from N and O; and
  each R$_3$ and R$_4$ is, independently, H, C$_1$–C$_{10}$ alkyl, a nitrogen protecting group, or R$_3$ and R$_4$, together, are a nitrogen protecting group;
  or R$_3$ and R$_4$ are joined in a ring structure that optionally includes an additional heteroatom selected from N and O.

In one embodiment $R_1$ is H, $C_1$–$C_{10}$ alkyl or $C_1$–$C_{10}$ substituted alkyl and $R_2$ is $C_1$–$C_{10}$ substituted alkyl. In another embodiment $R_1$ is $C_1$–$C_{10}$ alkyl. In a further embodiment $R_2$ is $C_1$–$C_{10}$ substituted alkyl and the substituent is $NH_3^+$ or $N(R_3)(R_4)$. In another embodiment $R_1$ and $R_2$ are both $C_1$–$C_{10}$ substituted alkyl with preferred substituents independently selected from $NH_3^+$ and $N(R_3)(R_4)$. In yet a further embodiment both $R_1$ and $R_2$ are $C_1$–$C_{10}$ alkyl.

In one embodiment $R_1$ and $R_2$ are joined in a ring structure that can include at least one heteroatom selected from N and O. Preferred ring structures are imidazole, piperidine, morpholine or a substituted piperazine with a preferred substituent being $C_1$–$C_{12}$ alkyl.

In one embodiment the heterocyclic base is a purine or a pyrimidine with preferred heterocyclic bases being adenine, cytosine, 5-methylcytosine, thymine, uracil, guanine or 2-aminoadenine.

In one embodiment the oligomeric compound comprises from about 5 to about 50 nucleosides. In a preferred embodiment the oligomeric compound comprises from about 8 to about 30 nucleosides with a preferred range from about 15 to about 25 nucleosides.

The present invention also includes nucleosidic compounds of the formula:

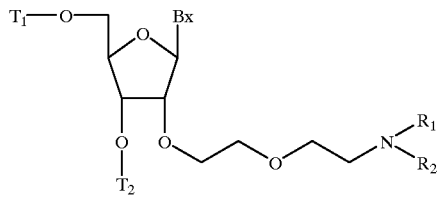

wherein:

Bx is a heterocyclic base;

$T_1$ and $T_2$, independently, are OH, a protected hydroxyl, an activated phosphorus group, a reactive group for forming an internucleotide linkage, a nucleoside, a nucleotide, an oligonucleoside an oligonucleotide or a linkage to a solid support;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, N $(R_3)(R_4)$, guanidino or acyl where said acyl is an acid, amide or an ester;

or $R_1$ and $R_2$, together, are a nitrogen protecting group or are joined in a ring structure that optionally includes an additional heteroatom selected from N and O; and each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O.

In one embodiment $R_1$ is H, $C_1$–$C_{10}$ alkyl or $C_1$–$C_{10}$ substituted alkyl and $R_2$ is $C_1$–$C_{10}$ substituted alkyl. In another embodiment $R_1$ is $C_1$–$C_{10}$ alkyl. In a further embodiment $R_2$ is $C_1$–$C_{10}$ substituted alkyl and the substituent is $NH_3^+$ or N $(R_3)(R_4)$. In another embodiment $R_1$ and $R_2$ are both $C_1$–$C_{10}$ substituted alkyl with preferred substituents independently selected from $NH_3^+$ and N $(R_3)(R_4)$. In yet a further embodiment both $R_1$ and $R_2$ are $C_1$–$C_{10}$ alkyl.

In one embodiment $R_1$ and $R_2$ are joined in a ring structure that can include at least one heteroatom selected from N and O. Preferred ring structures are imidazole, piperidine, morpholine or a substituted piperazine with a preferred substituent being $C_1$–$C_{12}$ alkyl.

In one embodiment the heterocyclic base is a purine or a pyrimidine with preferred heterocyclic bases being adenine, cytosine, 5-methylcytosine, thymine, uracil, guanine or 2-aminoadenine.

In one embodiment $T_1$ is a hydroxyl protecting group. In another embodiment $T_2$ is an activated phosphorus group or a connection to a solid support. A preferred solid support material is microparticles. With CPG being a more preferred solid support material.

DETAILED DESCRIPTION OF THE INVENTION

The present invention is directed to novel 2'-O-modified nucleosidic monomers and to oligomeric compounds incorporating these novel 2'-O-modified nucleosidic monomers. These modifications have certain desirable properties that contribute toward increases in binding affinity and/or nuclease resistance.

There are a number of items to consider when designing oligomeric compounds having enhanced binding affinities. One effective approach to constructing oligomeric compounds with very high RNA binding affinity relates to the combination of two or more different types of modifications, each of which contributes favorably to various factors that might be important for binding affinity.

Freier and Altmann, *Nucleic Acids Research*, (1997) 25:4429–4443, recently published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and $T_m$. Sugar modifications studied included substitutions on the 2'-position of the sugar, 3'-substitution, replacement of the 4'-oxygen, the use of bicyclic sugars, and four member ring replacements. Several heterocyclic base modifications were also studied including substitutions at the 5, or 6 position of thymine, modifications of pyrimidine heterocycles and modifications of purine heterocycles. Numerous backbone modifications were also investigated including backbones bearing phosphorus, backbones that did not bear a phosphorus atom, and backbones that were neutral.

Four general approaches potentially may be used to improve hybridization of oligonucleotides to RNA targets. These include: preorganization of the sugars and phosphates of the oligodeoxynucleotide strand into conformations favorable for hybrid formation, improving stacking of nucleobases by the addition of polarizable groups to the heterocycle bases of the nucleosidic monomers of the oligonucleotide, increasing the number of H-bonds available for A-U pairing, and neutralization of backbone charge to facilitate removing undesirable repulsive interactions. This invention principally employs the first of these, preorganization of the sugars and phosphates of the oligodeoxynucleotide strand into conformations favorable for hybrid formation, and can be used in combination with the other three approaches.

Sugars in DNA:RNA hybrid duplexes frequently adopt a C3' endo conformation. Thus, modifications that shift the conformational equilibrium of the sugar moieties in the single strand toward this conformation should preorganize the antisense strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This pucker conformation further assisted in increasing the Tm of the oligonucleotide with its target.

There is a clear correlation between substituent size at the 2'-position and duplex stability. Incorporation of alkyl substituents at the 2'-position typically leads to a significant decrease in binding affinity. Thus, small alkoxy groups generally are very favorable while larger alkoxy groups at the 2'-position generally are unfavorable. However, if the 2'-substituent contained an ethylene glycol motif, then a strong improvement in binding affinity to the target RNA is observed.

The high binding affinity resulting from 2'-substitution has been partially attributed to the 2'-substitution causing a C3' endo sugar pucker which in turn may give the oligomer a favorable A-form like geometry. This is a reasonable hypothesis since substitution at the 2' position by a variety of electronegative groups (such as fluoro and O-alkyl chains) has been demonstrated to cause C3' endo sugar puckering (De Mesmaeker et al., *Acc. Chem. Res.*, 1995, 28, 366–374; Lesnik et al., *Biochemistry*, 1993, 32, 7832–7838).

In addition, for 2'-substituents containing an ethylene glycol motif, a gauche interaction between the oxygen atoms around the O—C—C—O torsion of the side chain may have a stabilizing effect on the duplex (Freier et al., *Nucleic Acids Research*, (1997) 25:4429–4442). Such gauche interactions have been observed experimentally for a number of years (Wolfe et al., *Acc. Chem. Res.*, 1972, 5, 102; Abe et al., *J. Am. Chem. Soc.*, 1976, 98, 468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

The present invention has 2' side chain having the formula: 2'—OCH$_2$CH$_2$OCH$_2$CH$_2$N (R$_1$)(R$_2$), where R$_1$ and R$_2$ can each be alkyl or substituted alkyl groups which gives a tertiary amine capable of being protonated. When R$_1$ and R$_2$ are both methyl groups the pKa of the side chain is 9.0 to 10.0 (aliphatic saturated 3° amine). This tertiary amine is expected to be protonated at physiological pH (7.0), and in endosomes and lysosomes (pH 5.0). The resulting positive charge should improve the biostability of the drug by either inhibiting the nuclease from binding to the oligonucleotide or displacing the metal ions needed for the nucleases to carry on their function (Beese et al., *EMBO J.*, 1991, 10, 25–33; and Brautigam et al., *J. Mol. Bio.*, 1998, 277, 363–377).

As used herein, the term oligonucleoside includes oligomers or polymers containing two or more nucleoside subunits having a non-phosphorous linking moiety. Oligonucleosides according to the invention are monomeric subunits having a ribofuranose moiety attached to a heterocyclic base via a glycosyl bond. An oligonucleotide/nucleoside for the purposes of the present invention is a mixed backbone oligomer having at least two nucleosides covalently bound by a non-phosphate linkage and at least one phosphorous containing covalent bond with a nucleotide, and wherein at least one of the monomeric nucleotide or nucleoside units is a 2'-O-substituted compound prepared using the process of the present invention. An oligo-nucleotide/nucleoside can additionally have a plurality of nucleotides and nucleosides coupled through phosphorous containing and/or non-phosphorous containing linkages.

In the context of this invention, the term "oligomeric compound" refers to a plurality of nucleosides joined together in a specific sequence from naturally and non-naturally occurring nucleosides. The term includes oligonucleotides, oligonucleotide analogs, oligonucleosides having non-phosphorus containing internucleoside linkages and chimeric oligomeric compounds having mixed internucleoside linkages which can include all phosphorus or phosphorus and non-phosphorus containing internucleoside linkages. Each of the oligomeric compounds of the invention have at least one modified nucleoside where the modification is an aminooxy compound of the invention. Preferred nucleosides of the invention are joined through a sugar moiety via phosphorus linkages, and include adenine, guanine, adenine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine.

phosphorus containing linkages
phosphorodithioate (—O—P(S)(S)—O—);
phosphorothioate (—O—P(S)(O)—O—);
phosphoramidate (—O—P(O)(NJ)—O—);
phosphonate (—O—P(J)(O)—O—);
phosphotriesters (—O—P(O J)(O)—O—);
phophosphoramidate (—O—P(O)(NJ)—S—);
thionoalkylphosphonate (—O—P(S)(J)—O—);
thionoalkylphosphotriester (—O—P(O)(OJ)—S—);
boranophosphate (—R$^5$—P(O)(O)—J—);
non-phosphorus containing linkages
thiodiester (—O—C(O)—S—);
thionocarbamate (—O—C(O)(NJ)—S—);
siloxane (—O—Si(J)$_2$—O—);
carbamate (—O—C(O)—NH— and —NH—C(O)—O—)
sulfamate (—C—S(O)(O)—N— and —N—S(O)(O)—N—;
morpholino sulfamide (—O—S(O)(N(morpholino)—);
sulfonamide (—O—SO$_2$—NH—);
sulfide (—CH$_2$—S—CH$_2$—);
sulfonate (—O—SO$_2$—CH$_2$—);
N,N'-dimethylhydrazine (—CH$_2$—N(CH$_3$)—N(CH$_3$)—);
thioformacetal (—S—CH$_2$—O—);
formacetal (—O—CH$_2$—O—);
thioketal (—S—C(J)$_2$—O—); and
ketal (—O—C(J)$_2$—O—);
amine (—NH—CH$_2$—CH$_2$—);
hydroxylamine (—CH$_2$—N(J)—O—);
hydroxylimine (—CH=N—O—); and
hydrazinyl (—CH$_2$—N(H)—N(H)—).
where "J" denotes a substituent group which is commonly hydrogen or an alkyl group or a more complicated group that varies from one type of linkage to another.

In addition to linking groups as described above that involve the modification or substitution of the —O—P—

O— atoms of a naturally occurring linkage, included within the scope of the present invention are linking groups that include modification of the 5'-methylene group as well as one or more of the —O—P—O— atoms. Linkages of this type are well documented in the prior art and include without limitation the following:

amides (—CH$_2$—CH$_2$—N(H)—C(O)) and —CH$_2$—O—N=CH—; and alkylphosphorus (—C(J)$_2$—P(=O)(OJ)—C(J)$_2$—C(J)$_2$—).

wherein J is as described above.

Synthetic schemes for the synthesis of the substitute internucleoside linkages described above are disclosed in: WO 91/08213; WO 90/15065; WO 91/15500; WO 92/20822; WO 92/20823; WO 91/15500; WO 89/12060; EP 216860; U.S. Pat. Nos. 9,204,294; 9,003,138; 9,106,855; 9,203,385; 9,103,680; U.S. Pat. Ser. Nos. 07/990,848; 07/892,902; 07/806,710; 07/763,130; 07/690,786; U.S. Pat. Nos. 5,466,677; 5,034,506; 5,124,047; 5,278,302; 5,321,131; 5,519,126; 4,469,863; 5,455,233; 5,214,134; 5,470,967; 5,434,257; Stirchak, E. P., et al., *Nucleic Acid Res.*, 1989, 17, 6129–6141; Hewitt, J. M., et al., 1992, 11, 1661–1666; Sood, A., et al., *J. Am. Chem. Soc.*, 1990, 112, 9000–9001; Vaseur, J. J. et al., *J. Amer. Chem. Soc.*, 1992, 114, 4006–4007; Musichi, B., et al., *J. Org. Chem.*, 1990, 55, 4231–4233; Reynolds, R. C., et al., *J. Org. Chem.*, 1992, 57, 2983–2985; Mertes, M. P., et al., *J. Med. Chem.*, 1969, 12, 154–157; Mungall, W. S., et al., *J. Org. Chem.*, 1977, 42, 703–706; Stirchak, E. P., et al., *J. Org. Chem.*, 1987, 52, 4202–4206; Coull, J. M., et al., *Tet. Lett.*, 1987, 28, 745; and Wang, H., et al., *Tet. Lett.*, 1991, 32, 7385–7388.

The nucleosidic monomers and oligomeric compounds of the invention can include modified sugars and modified bases (see, e.g., U.S. Pat. No. 3,687,808 and PCT application PCT/US89/02323). Such oligomeric compounds are best described as being structurally distinguishable from, yet functionally interchangeable with, naturally occurring or synthetic wild type oligonucleotides. Representative modified sugars include carbocyclic or acyclic sugars, sugars having substituent groups at their 2' position, sugars having substituent groups at their 3' position, and sugars having substituents in place of one or more hydrogen atoms of the sugar. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. Nos. 5,138,045, 5,218,105, 5,223,618 5,359,044, 5,378,825, 5,386,023, 5,457,191, 5,459,255, 5,489,677, 5,506,351, 5,541,307, 5,543,507, 5,571,902, 5,578,718, 5,587,361, 5,587,469, all assigned to the assignee of this application. The disclosures of each of the above referenced publications are herein incorporated by reference.

Additional modifications may also be made at for example the 3' position of the sugar on the 3' terminal nucleosidic monomer and the 5' position of the 5' terminal nucleosidic monomer. In one aspect of the invention moieties or conjugates which enhance activity, cellular distribution or cellular uptake are chemically linked to one or more positions that are available for modification. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & nucleosidic monomers*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Representative heterocyclic bases amenable to the present invention include guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613. All such oligomeric compounds are comprehended by this invention.

The nucleosidic monomers used in preparing oligomeric compounds of the present invention can include appropriate activated phosphorus groups such as activated phosphate groups and activated phosphite groups. As used herein, the terms activated phosphate and activated phosphite groups refer to activated monomers or oligomers that are reactive with a hydroxyl group of another monomeric or oligomeric compound to form a phosphorus-containing internucleotide linkage. Such activated phosphorus groups contain activated phosphorus atoms in $p^{III}$ or $p^V$ valency states. Such activated phosphorus atoms are known in the art and include, but are not limited to, phosphoramdite, H-phosphonate and phosphate triesters. A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods to yield, in a preferred embodiment, phosphodiester or phosphorothioate internucleotide linkages. Additional activated phosphates and phosphites are disclosed in Tetrahedron Report Number 309 (Beaucage and Iyer, *Tetrahedron*, 1992, 48, 2223–2311).

A number of chemical functional groups can be introduced into compounds of the invention in a blocked form and subsequently deblocked to form a final, desired compound. Such groups can be introduced as groups directly or indirectly attached at the heterocyclic base and the sugar substituents at the 2', 3' and 5'-positions. In general, a blocking group renders a chemical functionality of a larger molecule inert to specific reaction conditions and can later be removed from such functionality without substantially damaging the remainder of the molecule (Green and Wuts, Protective Groups in Organic Synthesis, 2d edition, John Wiley & Sons, New York, 1991). For example, the nitrogen atom of amino groups can be blocked as phthalimido groups, as 9-fluorenylmethoxycarbonyl (FMOC) groups, and with triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine-9-yl (MOX). Chemical functional groups can also be "blocked" by including them in a precursor form. Thus, an azido group can be used considered as a "blocked" form of an amine since the azido group is easily converted to the amine. Further representative protecting groups utilized in oligonucleotide synthesis are discussed in Agrawal, et al., Protocols for Oligonucleotide Conjugates, Eds, Humana Press; New Jersey, 1994; Vol. 26 pp. 1–72.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p.1), and various substituted sulfonylethyl carbamates exemplified by the Nsc group (Samukov et al.,*Tetrahedron Lett*, 1994, 35:7821; Verhart and Tesser, *Rec. Trav. Chim. Pays-Bas*, 1987, 107:621).

Additional amino-protecting groups include but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl. Equivalents of these amino-protecting groups are also encompassed by the compounds and methods of the present invention.

In some especially preferred embodiments, one or more of the internucleoside linkages comprising oligomeric compounds of the invention are optionally protected phosphorothioate internucleoside linkages. Representative protecting groups for phosphorus containing internucleoside linkages such as phosphite, phosphodiester and phosphorothioate linkages include β-cyanoethyl, diphenylsilylethyl, δ-cyanobutenyl, cyano p-xylyl (CPX), N-methyl-N-trifluoro-acetyl ethyl (META), acetoxy phenoxy ethyl (APE) and butene-4-yl groups. See for example U.S. Pat. No. 4,725,677 and U.S. Pat. No. Re. 34,069 (β-cyanoethyl); Beaucage, S. L. and Iyer, R. P., *Tetrahedron*, 49 No. 10, pp. 1925–1963 (1993); Beaucage, S. L. and Iyer, R. P., *Tetrahedron*, 49 No. 46, pp. 10441–10488 (1993); Beaucage, S. L. and Iyer, R. P., *Tetrahedron*, 48 No. 12, pp. 2223–2311 (1992).

In the context of this specification, alkyl (generally $C_1$–$C_{20}$), alkenyl (generally $C_2$–$C_{20}$), and alkynyl (generally $C_2$–$C_{20}$) (with more preferred ranges from $C_1$–$C_{10}$ alkyl, $C_2$–$C_{10}$ alkenyl and $C_2$–$C_{10}$ alkynyl), groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylbutyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups. Representative alkyl substituents are disclosed in U.S. Pat. No. 5,212,295, at column 12, lines 41–50, hereby incorporated by reference in its entirety.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl compound, which has further straight or branched chains attached to the carbon atoms of the straight chain.

A cyclic compound, as used herein, refers to closed chain compounds, i.e. a ring of carbon atoms, such as an alicyclic or aromatic compound. The straight, branched, or cyclic compounds may be internally interrupted, as in alkoxy or heterocyclic compounds. In the context of this invention, internally interrupted means that the carbon chains may be interrupted with heteroatoms such as O, N, or S. However, if desired, the carbon chain may have no heteroatoms.

Compounds of the invention can include ring structures that include a nitrogen atom (e.g., —$N(R_1)$ ($R_2$) and —$N(R_3)$ ($R_4$) where ($R_1$) ($R_2$) and ($R_3$) ($R_4$) each form cyclic structures about the respective N to which they are attached). The resulting ring structure is a heterocycle or a heterocyclic ring structure that can include further heteroatoms selected from N, O and S. Such ring structures may be mono-, bi- or tricyclic, and may be substituted with substituents such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy. A preferred bicyclic ring structure that includes nitrogen is phthalimido.

In general, the term "hetero" denotes an atom other than carbon, preferably but not exclusively N, O, or S. Accordingly, the term "heterocyclic ring" denotes an alkyl ring system having one or more heteroatoms (i.e., non-carbon atoms). Heterocyclic ring structures of the present invention can be fully saturated, partially saturated, unsaturated or with a polycyclic heterocyclic ring each of the rings may be in any of the available states of saturation. Heterocyclic ring structures of the present invention also include heteroaryl which includes fused systems including systems where one or more of the fused rings contain no heteroatoms. Heterocycles, including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

In the context of this specification, aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

Oligomeric compounds according to the present invention that are hybridizable to a target nucleic acid preferably comprise from about 5 to about 50 nucleosides. It is more preferred that such compounds comprise from about 8 to about 30 nucleosides, with 15 to 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule.

It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

The oligomeric compounds of the present invention can be used in diagnostics, therapeutics and as research reagents. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes RNA-DNA transcription or RNA-protein translation as a fundamental part of its hereditary, metabolic or cellular control is susceptible to therapeutic and/or prophylactic treatment in accordance with this invention. Seemingly diverse organisms such as bacteria, yeast, protozoa, algae, all plants and all higher animal forms including warm-blooded animals, ca be treated. Further each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligomeric compounds. As used herein, therapeutics is meant to include the eradication of a disease state, by killing an organism or by control of erratic or harmful cellular growth or expression.

Oligomeric compounds according to the invention can be assembled in solution or through solid-phase reactions, for example, on a suitable DNA synthesizer utilizing nucleosides, phosphoramidites and derivatized controlled pore glass (CPG) according to the invention and/or standard nucleosidic monomer precursors. In addition to nucleosides that include a novel modification of the inventions other nucleoside within an oligonucleotide may be further modified with other modifications at the 2' position. Precursor nucleoside and nucleosidic monomer precursors used to form such additional modification may carry substituents either at the 2' or 3' positions. Such precursors may be synthesized according to the present invention by reacting appropriately protected nucleosides bearing at least one free 2' or 3' hydroxyl group with an appropriate alkylating agent such as, but not limited to, alkoxyalkyl halides, alkoxylalkylsulfonates, hydroxyalkyl halides, hydroxyalkyl sulfonates, aminoalkyl halides, aminoalkyl sulfonates, phthalimidoalkyl halides, phthalimidoalkyl sulfonates, alkylaminoalkyl halides, alkylaminoalkyl sulfonates, dialkylaminoalkyl halides, dialkylaminoalkylsulfonates, dialkylaminooxyalkyl halides, dialkylaminooxyalkyl sulfonates and suitably protected versions of the same. Preferred halides used for alkylating reactions include chloride, bromide, fluoride and iodide. Preferred sulfonate leaving groups used for alkylating reactions include, but are not limited to, benzenesulfonate, methylsulfonate, tosylate, p-bromobenzenesulfonate, triflate, trifluoroethylsulfonate, and (2,4-dinitroanilino)-benzenesulfonate.

Suitably protected nucleosides can be assembled into oligomeric compounds according to known techniques. See, for example, Beaucage et al., *Tetrahedron*, 1992, 48, 2223.

The ability of oligomeric compounds to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands. The structure-stability relationships of a large number of nucleic acid modifications have been reviewed (Freier and Altmann, *Nucl. Acids Research*, 1997, 25, 4429–443).

The relative binding ability of the oligomeric compounds of the present invention was determined using protocols as described in the literature (Freier and Altmann, *Nucl. Acids*

Research, 1997, 25, 4429–443). Typically absorbance versus temperature curves were determined using samples containing 4 uM oligonucleotide in 100 mM Na+, 10 mM phosphate, 0.1 mM EDTA, and 4 uM complementary, length matched RNA.

The in vivo stability of oligomeric compounds is an important factor to consider in the development of oligonucleotide therapeutics. Resistance of oligomeric compounds to degradation by nucleases, phosphodiesterases and other enzymes is therefore determined. Typical in vivo assessment of stability of the oligomeric compounds of the present invention is performed by administering a single dose of 5 mg/kg of oligonucleotide in phosphate buffered saline to BALB/c mice. Blood collected at specific time intervals post-administration is analyzed by HPLC or capillary gel electrophoresis (CGE) to determine the amount of the oligomeric compound remaining intact in circulation and the nature the of the degradation products.

Additional objects, advantages, and novel features of this invention will become apparent to those skilled in the art upon examination of the following examples, which are not intended to be limiting. All oligonucleotide sequences are listed in a standard 5' to 3' order from left to right.

EXAMPLE 1

2'-O-[2(2-N,N-dimethylaminoethoxy)ethyl]-5-methyl uridine

2[2-(Dimethylamino)ethoxy]ethanol (Aldrich, 6.66 g, 50 mmol) was slowly added to a solution of borane in tetrahydrofuran (1 M, 10 mL, 10 mmol) with stirring in a 100 mL bomb. Hydrogen gas evolved as the solid dissolved $O^2$-,2'-anhydro-5-methyluridine (1.2 g, 5 mmol), and sodium bicarbonate (2.5 mg) were added and the bomb was sealed, placed in an oil bath and heated to 155° C. for 26hours. The bomb was cooled to room temperature and opened. The crude solution was concentrated and the residue partitioned between water (200 mL) and hexanes (200 mL). The excess alcohol was extracted into the hexane layer. The aqueous layer was extracted with ethyl acetate (3×200 mL) and the combined organic layers were washed once with water, dried over anhydrous sodium sulfate and concentrated. The residue was columned on silica gel using methanol/methylene chloride 1:20 (which has 2% triethylamine) as the eluent. As the column fractions were concentrated a colorless solid formed which was collected to give 490 mg of the title compound as a white solid. Rf=0.56 in $CH_2$—$CH_{12}$:$CH_3$—OH (10:1); MS/ES calculated 374; observed 374.5.

EXAMPLE 2

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) were added and stirred for 1 hour. The reaction mixture was poured into water (200 mL) and extracted with $CH_2Cl_2$ (2×200 mL). The combined $CH_2Cl_2$ layers were washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gave 0.72 g (82%) of the title compound.

EXAMPLE 3

5'-O-Dimethoxytrityl-2'-O-[2(2-N,N-dimethylaminoethoxy)ethyl)]-5-methyl uridine-3'-O-(cyanoethyl-N,N-diisopropyl) phosphoramidate Diisopropylaminotetrazolide (0.6 g) and 2-cyanoethoxy-N,N-diisopropyl phosphoramidite (1.1 mL, 2 eq.) were added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture was stirred overnight and the solvent evaporated. The resulting residue was purified by silica gel flash column chromatography with ethyl acetate as the eluent to give 1.98 g (83% yield) of the title compound.

EXAMPLE 4

5'-O-Dimethoxytrityl-2'-O-[2(2-N,N-dimethylaminoethoxy)ethyl)]-5-methyl-uridine-3'-O-succinate 5'-O-Dimethoxytrityl-2'-O-[2(2-N,N-dimethylaminoethoxy)ethyl)]-5-methyluridine (270 mg, 0.41 mmol) was heated with 68 mg of succinic anhydride (0.6 mmol), 4-N,N-dimethylamino pyridine (24 mg) and $Et_3N$ (56 μL) in dichloroethane (1 mL) at 50° C. for 10 minutes in a Pyrex tube in a heating block. After cooling, the reaction mixture was diluted with methylene chloride (20 mL) and washed with a 10% aqueous solution of citric acid (3×20 mL) followed by water. The resulting solution was dried over anhydrous $Na_2SO_4$ to give 217 mg (58% yield) of the title compound.

TLC indicated ($CH_2Cl_2$/MeOH, 10:1) a polar product at the origin, as expected.

EXAMPLE 5

5'-O-Dimethoxytrityl-2'-O -[2(2-N,N-dimethylaminoethoxy)ethyl)]-5-methyl-uridine-3'-O-succinyl controlled pore glass (CPG)

5'-O-Dimethoxytrityl-2'-O-[2(2-N,N-dimethylaminoethoxy)ethyl)]-5-methyl-uridine-3'-O-succinate (116 mg, 0.15 mmol, 2 eq.) was dried under high vacuum overnight. To this dried material was added CPG (650 mg, 1 eq.), anhydrous DMF (2 mL), N-methylmorpholine (33 μL, 4 eq.) and 2-1H-benzotriazole-1-yl 2-1H-benzotriazole-1-yl-1,1,3,3-tetramethyluronium-tetrafluoro-borate (TBTU, 48 mg, 2 eq.) was added to the reaction mixture with shaking for 12 hours. The CPG was then filtered and washed with DMF, $CH_2Cl_2$, $CH_3CN$ and $Et_2O$. Finally, it was dried and capped with acetic anhydride/$Et_3N$. The loading of the CPG was determined via the dimethoxytrityl assay method to be 53 μmoles/g.

EXAMPLE 6

2-[2-(dimethylamino)ethylmercapto]ethanol 2-(Dimethylamino)ethanethiol hydrochloride (Aldrich) is treated with NaOH (0.2N) in ethanol (95%). To this slurry, 2-bromoethanol (1.2 eq.) is added and the mixture is refluxed for 2 hours. The reaction mixture is cooled, filtered and concentrated. The resultant residue is purified by silica gel flash column chromatography to give the title compound.

EXAMPLE 7

2'-O-[2-[2-((dimethylamino)ethyl)mercapto]ethyl]-5-methyl uridine

2-[2-((dimethylamino)ethyl)mercapto] ethanol (50 mmol) is slowly added to a solution of borane in tetrahydrofuran (1 M, 10 mL, 10 mmol) with stirring in a 100 mL bomb. Hydrogen gas is evolved as the solid dissolves. $O^2$, 2'-anhydro-5-methyluridine (1.2 g, 5 mmol), and sodium bicarbonate (2.5 mg) are added and the bomb is sealed, then placed in an oil bath and heated to 155° C. for 26 hours. The bomb is cooled to room temperature and opened. The crude solution is concentrated and the residue partitioned between water (200 mL) and hexanes (200 mL). The excess phenol is extracted into hexanes. The aqueous layer is extracted with ethyl acetate (3×200 mL) and the combined organic layer is washed once with water and dried over anhydrous sodium sulfate and concentrated. The resultant residue is purified by silica gel flash column chromatography using methanol/methylene chloride having 2% triethylamine to give the title compound.

EXAMPLE 8

5'-O-Dimethoxytrityl-2'-O-2-[2-((dimethylamino) ethyl)mercapto]ethyl)]5-methyl uridine To 2'-O-2-[2-((dimethylamino)ethyl)mercapto]ethyl)]5-methyl uridine (1.3 mmol) in anhydrous pyridine (8 mL), triethylamine (0.36 mL) and DMT-Cl (0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, saturated NaCl solution, dried over anhydrous sodium sulfate and concentrated. The resultant residue is purified by silica gel flash column chromatography using methanol/methylene chloride having 1% triethylamine to give the title compound.

EXAMPLE 9

5'-O-Dimethoxytrityl-2'-O-2-[2-((dimethylamino) ethyl)mercapto]ethyl)]5-methyl uridine-3'-O-(cyanoethyl-N,N-diisopropyl) phosphoramidate 5'-O-Dimethoxytrityl-2'-O-2-[2-((dimethylamino)ethyl) mercapto]ethyl)]5-methyluridine (3 mmol) is dissolved in $CH_2Cl_2$ (20 mL) and to this solution, under argon, diisopropylaminotetrazolide (0.6 g) and 2-cyanoethoxy-N,N-diisopropyl phosphoramidite (1.1 mL, 2 eq.) are added. The reaction is stirred overnight and the solvent is evaporated. The resultant residue is purified by silica gel flash column chromatography using ethyl acetate to give the title phosphoramidite.

EXAMPLE 10

5'-O-Dimethoxytrityl-2'-O-2-[2-((dimethylamino) ethyl)mercapto]ethyl)]5-methyl-uridine-3'-O-succinate 5'-O-Dimethoxytrityl-2'-O-2-[2-((dimethylamino)ethyl) mercapto]ethyl)]5-methyluridine (0.41 mmol) is heated with succinic anhydride (68 mg, 0.6 mmol), 4-N,N-dimethylamino pyridine (24 mg) and $Et_3N$ (56 µL) in dichloroethane (1 mL) at 50° C. for 10 minutes in a Pyrex tube in a heating block. After cooling the reaction mixture is diluted with methylene chloride (20 mL) and washed with 10% citric acid aqueous solution (3×20 mL) followed by water and dried over anhydrous $Na_2SO_4$ to give the title succinate.

EXAMPLE 11

5'-O-Dimethoxytrityl-2'-O-2-[2-((dimethylamino) ethyl)mercapto]ethyl)]5-methyl-uridine-3'-O-succinyl controlled pore glass (CPG)

The succinate from Example 10 above (0.15 mmol, 2 eq.) is dried under vacuum overnight. CPG (650 mg, 1 eq.), anhydrous DMF (2 mL), 33 µL of N-methylmorpholine (4 eq.) and 48 mg (2 eq.) of TBTU (2-1H-benzotriazole-1-yl) are added to the dried succinate. 1,1,3,3-tetramethyluronium-tetrafluoroborate is added and the mixture is shaken for 12 hours. The CPG is then filtered and washed with DMF, $CH_2Cl_2$, $CH_3CN$ and $Et_2O$. The CPG is dried and capped with acetic anhydride/$Et_3N$. The loading is determined using the standard dimethoxytrityl assay.

EXAMPLE 12

2-[2-(diethylamino)ethoxy] ethanol 2-(2-aminoethoxy)ethanol (Aldrich 0.5 mmol) is treated with $NaBH_3CN$ (Aldrich, 200 mg, 3.0 mmol) in 50% aqueous methanol (30 mL). To this solution, acetaldehyde 95% purity (2 mL, 17 mmol) is added in one portion and the mixture is heated at 50° C. for 2 days in a flask under argon. After removal of the solvent under reduced pressure, the residue is dissolved in water, extracted with ethylacetate to give the title compound.

EXAMPLE 13

2'-O-[2(2-N,N-diethylaminoethoxy)ethyl]-5-methyl uridine

2[2-(Diethylamino)ethoxy]ethanol (50 mmol) is slowly added to a solution of borane in tetrahydrofuran (1 M, 10 mL, 10 mmol) with stirring in a 100 mL bomb. Hydrogen gas evolves as the solid dissolves $O^2$-2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess alcohol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. The appropriate column fractions are concentrated and concentrated to give the title compound.

EXAMPLE 14

5'-O-dimethoxytrityl-2'-O-[2(2-N,N-diethylaminoethoxy)ethyl)]-5-methyl uridine

To 1.3 mmol of 2'-O-[2(2-N,N-diethylaminoethoxy) ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

EXAMPLE 15

5'-O-Dimethoxytrityl-2'-O-[2(2-N,N-diethylaminoethoxy)ethyl)]-5-methyluridine-3'-O-(cyanoethyl-N,N-diisopropyl) phosphoramidate Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-diethylaminoethoxy)ethyl)]-5-methyluridine (3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give title compound.

EXAMPLE 16

5'-O-Dimethoxytrityl-2'-O-[2(2-N,N-diethylaminoethoxy)ethyl)]-5-methyl-uridine-3'-O-succinate 5'-O-Dimethoxytrityl-2'-O-[2(2-N,N-diethylaminoethoxy)ethyl)]-5-methyluridine (0.41 mmol) is heated with 68 mg of succinic anhydride (0.6 mmol), 4-N,N-diethylamino pyridine (24 mg) and Et$_3$N (56 µL) in dichloroethane (1 mL) at 50° C. for 10 minutes in a Pyrex tube in a heating block. After cooling, the reaction mixture is diluted with methylene chloride (20 mL) and washed with a 10% aqueous solution of citric acid (3×20 mL) followed by water. The resulting solution is dried over anhydrous Na$_2$SO$_4$ to give the title compound.

EXAMPLE 17

5'-O-Dimethoxytrityl-2'-O-[2(2-N,N-diethylaminoethoxy)ethyl)]-5-methyl-uridine-3'-O-succinyl controlled pore glass (CPG)

5'-O-Dimethoxytrityl-2'-O-[2(2-N,N-diethylaminoethoxy)ethyl)]-5-methyl-uridine-3'-O-succinate (0.15 mmol, 2 eq.) is dried under high vacuum overnight. To this dried material is added CPG (650 mg, 1 eq.), anhydrous DMF (2 mL), N-methylmorpholine (33 µL, 4 eq.) and 2-1H-benzotriazole-1-yl- 1,1,3,3-tetramethyluroniumtetrafluoroborate (TBTU, 48 mg, 2 eq.) is added to the reaction mixture with shaking for 12 hours. The CPG is then filtered and washed with DMF, CH$_2$Cl$_2$, CH$_3$CN and Et$_2$O. Finally, it is dried and capped with acetic anhydride/Et$_3$N. The loading of the CPG is determined via the dimethoxytrityl assay method.

EXAMPLE 18

2-[bis-2-(N,N-dimethylamino-ethyl)amino ethoxy] ethanol

N,N-Dimethylaminoacetaldehyde diethyl acetal (Aldrich, 1 mmol) is treated with aqueous solution of trifluoroacetic acid and refluxed overnight to give N,N-dimethylamino acetaldehyde. 2-(2-Aminoethoxy)ethanol is treated with NaBH$_3$CN and N,N-dimethylamino acetaldehyde in methanol solvent and refluxed over night. After removal of the solvent under reduced pressure, the residue is dissolved in water, extracted with ethyl acetate and purified by column chromatography to give the title compound.

EXAMPLE 19

2'-O-[2(bis-2-N,N-dimethylaminoethyl)ethoxy) ethyl]-5-methyl uridine

2[2-(Bis-N,N-dimethylaminomethyl)ethoxy]ethanol (50 mmol) is slowly added to a solution of borane in tetrahydrofuran (1 M, 10 mL, 10 mmol) with stirring in a 100 mL bomb. Hydrogen gas evolves as the solid dissolves O$^2$-2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess alcohol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. The column fractions are concentrated to give the title compound.

EXAMPLE 20

5'-O-Dimethoxytrityl-2'-O-[2(2-(bis-N,N-dimethylaminoethyl)ethoxy)ethyl)]-5-methyl uridine To 1.3 mmol of 2'-O-[2(2-(bis-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added with stirring for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

EXAMPLE 21

5'-O-Dimethoxytrityl-2'-O-[2(2-(bis-N,N-dimethylaminoethyl)ethoxy)ethyl)]-5-methyl uridine-3'-O-(cyanoethyl-N,N-diisopropyl) phosphoramidate Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-(bis-N,N-dimethylaminoethyl)ethoxy)ethyl)]-5-methyluridine (3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give title compound.

EXAMPLE 22

5'-O-Dimethoxytrityl-2'-O-[2(2-bis(N,N-dimethylaminoethyl)ethoxy)ethyl)]-5-methyl-uridine-3'-O-succinate 5'-O-Dimethoxytrityl-2'-O-[2(2-bis-N,N-dimethylaminoethylethoxy)ethyl)]-5-methyluridine (0.41 mmol) is heated with 68 mg of succinic anhydride (0.6 mmol), 4-N,N-dimethylaminoethyl pyridine (24 mg) and Et$_3$N (56 µL) in dichloroethane (1 mL) at 50° C. for 10 minutes in a Pyrex tube in a heating block. After cooling, the reaction mixture is diluted with methylene chloride (20 mL) and washed with a 10% aqueous solution of citric acid (3×20 mL) followed by water. The resulting solution is dried over anhydrous Na$_2$SO$_4$ to give the title compound.

EXAMPLE 23

5'-O-Dimethoxytrityl-2'-O-[2(2-bis(N,N-dimethylaminoethyl-ethoxy)ethyl)]-5-methyl-uridine-3'-O-succinyl controlled pore glass (CPG)

5'-O-Dimethoxytrityl-2'-O-[2(2-bis-N,N-dimethylaminoethylethoxy)ethyl)]-5-methyl-uridine-3'-O-succinate (0.15 mmol, 2 eq.) is dried under high vacuum overnight. To this dried material is added CPG (650 mg, 1 eq.), anhydrous DMF (2 mL), N-methylmorpholine (33 µL, 4 eq.) and 2-1H-benzotriazole-1-yl- 1,1,3,3-tetramethyluroniumtetrafluoro-borate (TBTU, 48 mg, 2 eq.)

is added to the reaction mixture with shaking for 12 hours. The CPG is then filtered and washed with DMF, $CH_2Cl_2$, $CH_3CN$ and $Et_2O$. Finally, it is dried and capped with acetic anhydride/$Et_3N$. The loading of the CPG is determined via the dimethoxytrityl assay method.

EXAMPLE 24

General procedures for oligonucleotide synthesis

Oligomeric compounds are synthesized on a PerSeptive Biosystems Expedite 8901 Nucleic Acid Synthesis System. Multiple 1-mmol syntheses are performed for each oligonucleotide. The 3'-end nucleoside containing solid support is loaded into the column. Trityl groups are removed with trichloroacetic acid (975 mL over one minute) followed by an acetonitrile wash. The oligonucleotide is built using a modified diester or thioate protocol.

Phosphodiester protocol All standard amidites (0.1 M) are coupled over a 1.5 minute time frame, delivering 105 µL material. All novel amidites are dissolved in dry acetonitrile (100 mg of amidite/1 mL acetonitrile) to give approximately 0.08–0.1 M solutions. The 2'-modified amidite is double coupled using 210 µL over a total of 5 minutes. Total coupling time is approximately 5 minutes (210 mL of amidite delivered). 1-H-tetrazole in acetonitrile is used as the activating agent. Excess amidite is washed away with acetonitrile. (1S)-(+)-(10-camphorsulfonyl) oxaziridine (CSO, 1.0 g CSO/8.72 mL dry acetonitrile) is used to oxidize (3 minute wait step) delivering approximately 375 µL of oxidizer. Standard amidites are delivered (210 µL) over a 3-minute period.

Phosphorothioate protocol

The 2'-modified amidite is double coupled using 210 µL over a total of 5 minutes. The amount of oxidizer, 3H-1,2-benzodithiole-3-one-1,1-dioxide (Beaucage reagent, 3.4 g Beaucage reagent/200 mL acetonitrile), is 225 µL (one =minute wait step). The unreacted nucleoside is capped with a 50:50 mixture of tetrahydrofuran/acetic anhydride and tetrahydrofuran/pyridine/1-methyl imidazole. Trityl yields are followed by the trityl monitor during the duration of the synthesis. The final DMT group is left intact. After the synthesis, the contents of the synthesis cartridge (1 mmole) is transferred to a Pyrex vial and the oligonucleotide is cleaved from the controlled pore glass (CPG) using 30% ammonium hydroxide ($NH_4OH$, 5 mL) for approximately 16 hours at 55° C.

Oligonucleotide Purification

After the deprotection step, the samples are filtered from CPG using Gelman 0.45 µm nylon acrodisc syringe filters. Excess $NH_4H$ is evaporated away in a Savant AS160 automatic speed vac. The crude yield is measured on a Hewlett Packard 8452A Diode Array Spectrophotometer at 260 nm. Crude samples are then analyzed by mass spectrometry (MS) on a Hewlett Packard electrospray mass spectrometer. Trityl-on oligomeric compounds are purified by reverse phase preparative high performance liquid chromatography (HPLC). HPLC conditions are as follows: Waters 600E with 991 detector; Waters Delta Pak C4 column (7.8×300 mm); Solvent A: 50 mM triethylammonium acetate (TEA-Ac), pH 7.0; Solvent B: 100% acetonitrile; 2.5 mL/min flow rate; Gradient: 5% B for first five minutes with linear increase in B to 60% during the next 55 minutes. Fractions containing the desired product/s (retention time=41 minutes for DMT-ON-16314; retention time=42.5 minutes for DMT-ON-16315) are collected and the solvent is dried off in the speed vac. Oligomeric compounds are detritylated in 80% acetic acid for approximately 60 minutes and lyophilized again. Free trityl and excess salt are removed by passing detritylated oligomeric compounds through Sephadex G-25 (size exclusion chromatography) and collecting appropriate samples through a Pharmacia fraction collector. The solvent is again evaporated away in a speed vac. Purified oligomeric compounds are then analyzed for purity by CGE, HPLC (flow rate: 1.5 mL/min; Waters Delta Pak C4 column, 3.9×300 mm), and MS. The final yield is determined by spectrophotometer at 260 nm.+

Procedures

Procedure 1

ICAM-1 Expression

Oligonucleotide Treatment of HUVECs: Cells were washed three times with Opti-MEM (Life Technologies, Inc.) prewarmed to 37° C. Oligomeric compounds were premixed with 10 µg/mL Lipofectin (Life Technologies, Inc.) in Opti-MEM, serially diluted to the desired concentrations, and applied to washed cells. Basal and untreated (no oligonucleotide) control cells were also treated with Lipofectin. Cells were incubated for 4 h at 37° C., at which time the medium was removed and replaced with standard growth medium with or without 5 mg/mL TNF-A α ® & D Systems). Incubation at 37° C. was continued until the indicated times.

Quantitation of ICAM-1 Protein Expression by Fluorescence-activated Cell Sorter: Cells were removed from plate surfaces by brief trypsinization with 0.25% trypsin in PBS. Trypsin activity was quenched with a solution of 2% bovine serum albumin and 0.2% sodium azide in PBS (+Mg/Ca). Cells were pelleted by centrifugation (1000 rpm, Beckman GPR centrifuge), resuspended in PBS, and stained with 3 µl/$10^5$ cells of the ICAM-1 specific antibody, CD54-PE (Pharmingin). Antibodies were incubated with the cells for 30 min at 4° C. in the dark, under gently agitation. Cells were washed by centrifugation procedures and then resuspended in 0.3 mL of FacsFlow buffer (Becton Dickinson) with 0.5% formaldehyde (Polysciences). Expression of cell surface ICAM-1 was then determined by flow cytometry using a Becton Dickinson FACScan. Percentage of the control ICAM-1 expression was calculated as follows: [(oligonucleotide-treated ICAM-1 value)-(basal ICAM-1 value)/(non-treated ICAM-1 value)-(basal ICAM-1 value)]. (Baker, Brenda, et. al. 2'-O-(2-Methoxy)ethyl-modified Anti-intercellular Adhesion Molecule 1 (ICAM-1) Oligomeric compounds Selectively Increase the ICAM-1 mRNA Level and Inhibit Formation of the ICAM-1 Translation Initiation Complex in Human Umbilical Vein Endothelial Cells, *The Journal of Biological Chemistry*, 272, 11994–12000, 1997.)

ICAM-1 expression of 2'-O-[2-(2-N,N-dimethylaminoethyl)oxyethyl]-5-methyl modified oligomeric compounds of the invention is measured by the reduction of ICAM-1 levels in treated HUVEC cells. The oligomeric compounds are believed to work by a direct binding RNase H independent mechanism. Appropriate scrambled control oligomeric compounds are used as controls. They have the same base composition as the test sequence.

Sequences that contain the 2'-O-[2-(2-N,N-dimethylaminoethyl)oxyethyl]-5-methyl modification as listed in Table 1 below are prepared and tested in the above assay. SEQ ID NO: 3, a C-raf targeted oligonucleotide, is used as a control.

TABLE 1

Oligomeric compounds Containing 2'-O-[2-(2-N,N-dimethyl aminoethyl)oxyethyl]-5-methyl modification

| SEQ ID NO: | Sequence (5'-3') | Target |
|---|---|---|
| 1 | 5'-$T_sC^m_sT_sG_sA_sG_sT_sA_sG_sC^m_s$ $A_sG_sA_sG_sG_sA_sG_sC^m_sT_sC$-3' | Human ICAM-1 |
| 2 | 5'-$T_oC^m_oT_oG_oA_oG_oT_oA_oG_oC^m_o$ $A_oG_oA_oG_oG_oA_oG_oC^m_oT_oC$-3' | Human ICAM-1 |
| 3 | 5'-$A_sT_sG_sC^m_sA_sT_sT_sC_s{}^mT_sG_sC_s{}^mC_s{}^mC_s{}^mC^m_s$ $C^m_sA_sA_sG_sG_sA$-3' | mouse C-raf |
| 4 | 5'-$G_sC^m_sC^m_sC^m_sA_sA_sG_sC^m_sT_sG_sG_sC^m_s$ $A_sT_sC^m_sC^m_sG_sT_sC^m_sA$-3' | Human ICAM-1 |

All nucleosides in bold are 2'-O-[2-(2-N,N-dimethylaminoethyl)oxyethyl]-5-methyl; subscript S indicates a phosphorothioate linkage; subscript O indicates a phosphodiester linkage; and a superscript m on a C ($C^m$) indicates a 5-methyl-C.

Procedure 2
Enzymatic Degradation of 2'-O-modified Oligomeric Compounds

Three oligomeric compounds are synthesized incorporating the modifications to the 3' nucleoside at the 2'-O-position (Table 2). These modified oligomeric compounds are subjected to snake venom phosphodiesterase to determine their nuclease resistance. Oligomeric compounds (30 nanomoles) are dissolved in 20 mL of buffer containing 50 mM Tris-HCl pH 8.5, 14 mM $MgCl_2$, and 72 mM NaCl. To this solution 0.1 units of snake-venom phosphodiesterase (Pharmacia, Piscataway, N.J.), 23 units of nuclease P1 (Gibco LBRL, Gaithersberg, Md.), and 24 units of calf intestinal phosphatase (Boehringer Mannheim, Indianapolis, Ind.) are added and the reaction mixture is incubated at 37° C. for 100 hours. HPLC analysis is carried out using a Waters model 715 automatic injector, model 600E pump, model 991 detector, and an Alltech (Alltech Associates, Inc., Deerfield, Ill.) nucleoside/nucleotide column (4.6×250 mm). All analyses are performed at room temperature. The solvents used are A: water and B: acetonitrile. Analysis of the nucleoside composition is accomplished with the following gradient: 0–5 min., 2% B (isocratic); 5–20 min., 2% B to 10% B (linear); 20–40 min., 10% B to 50% B. The integrated area per nanomole is determined using nucleoside standards. Relative nucleoside ratios are calculated by converting integrated areas to molar values and comparing all values to thymidine, which is set at its expected value for each oligomer.

TABLE 2

Relative Nuclease Resistance of 2'-Modified Chimeric Oligomeric compounds
SEQ ID NO 5; 5'-TTT TTT TTT TTT TTT T*T*T*T*-3' (Uniform phosphodiester)

| T* = 2'-modified T | 2'-O-Modification |
|---|---|
| —O—$CH_2$—$CH_2$—$CH_3$ | Pr |
| —O—$CH_2$—$CH_2$—O—$CH_3$ | MOE |
| —O—(DMAEOE) | DMAEOE |

Procedure 3
General Procedure for the Evaluation of Gapped 2'-O-DMAEOE Modified Oligomeric Compounds Targeted to Ha-ras Different types of human tumors, including sarcomas, neuroblastomas, leukemias and lymphomas, contain active oncogenes of the ras gene family. Ha-ras is a family of small molecular weight GTPases whose function is to regulate cellular proliferation and differentiation by transmitting signals resulting in constitutive activation of ras are associated with a high percentage of diverse human cancers. Thus, ras represents an attractive target for anticancer therapeutic strategies.

SEQ ID NO: 6 is a 20-base phosphorothioate oligodeoxynucleotide targeting the initiation of translation region of human Ha-ras and it is a potent isotype-specific inhibitor of Ha-ras in cell culture based on screening assays ($IC_{50}$=45 nm). Treatment of cells in vitro with SEQ ID NO: 6 results in a rapid reduction of Ha-ras mRNA and protein synthesis and inhibition of proliferation of cells containing an activating Ha-ras mutation. When administered at doses of 25 mg/kg or lower by daily intraperitoneal injection (IP), SEQ ID NO: 6 exhibits potent antitumor activity in a variety of tumor xenograft models, whereas mismatch controls do not display antitumor activity. SEQ ID NO: 6 has been shown to be active against a variety of tumor types, including lung, breast, bladder, and pancreas in mouse xenograft studies (Cowsert, L. M. *Anti-cancer drug design*, 1997, 12, 359–371). A second-generation analog of SEQ ID NO: 6, where the 5' and 3' termini ("wings") of the sequence are modified with 2'-methoxyethyl (MOE) modification and the backbone is kept as phosphorothioate (Table 2, SEQ ID NO: 12), exhibits $IC_{50}$ of 15 nm in cell culture assays. Thus, a 3-fold improvement in efficacy is observed from this chimeric analog. Because of the improved nuclease resistance of the 2'-MOE phosphorothioate, SEQ ID NO: 12 increases the duration of antisense effect in vitro. This will relate to frequency of administration of this drug to cancer patients. SEQ ID NO: 12 is currently under evaluation in ras dependent tumor models (Cowsert, L. M. *Anti-cancer drug design*, 1997, 12, 359–371). The parent compound, SEQ ID NO: 6, is in Phase I clinical trials against solid tumors by systemic infusion. Antisense oligomeric compounds having the 2'-O-DMAEOE modification are prepared and tested in the aforementioned assays in the manner described to determine activity. Oligomeric compounds that are initially prepared are listed in Table 3 below.

TABLE 3

Ha-ras Antisense Oligomeric compounds With 2'-O-DMAEOE Modifications and Their Controls

| SEQ ID NO: | Sequence | Back-bone | 2'-Modif. | Comments |
|---|---|---|---|---|
| 6 | 5'-TsCsCs GsTsCs AsTsCs Gs CsTs CsCsTs CsAsGs GsG-3' | P=S | 2'-H | parent |
| 7 | 5'-TsCsAs GsTsAs AsTsAs Gs GsCs CsCsAs CsAsTs GsG-3' | P=S | 2'-H | mismatch control |
| 8 | 5'-ToToCo <u>GsTsCs AsTsCs Gs CsTs</u> CoCoTo CoAoGo GoG-3' | P=O/ P=S/ P=S | 2'-O-DMAEOE in the back-wings bone) | Gapmer (mixed |
| 9 | 5'-TsCsCs <u>GsTsCs AsTsCs Gs CsTs</u> CsCsTs CsAsGs GsG-3' | P=S | 2'-O-DMAEOE as in the uniform wings thioate | Gapmer |
| 10 | 5'-ToCoAo <u>GsTsAs AsTsAs GsCsCs GsCsCs Gs</u> Co Co CoCoAo CoAoTo GoG-3' | P=O/ P=S/ P=O | 2'-O-DMAEOE in the back-wings bone) | Gapmer (mixed |

TABLE 3-continued

Ha-ras Antisense Oligomeric compounds With
2'-O-DMAEOE Modifications and Their Controls

| SEQ ID NO: | Sequence | Back-bone | 2'-Modif. | Comments |
|---|---|---|---|---|
| 11 | 5'-TsCsAs <u>GsTsAs AsTs As GsCsCs</u> GsCsCs CsCsAs CsAsTs GsC-3' | P=S | 2'-O-DMAEOE | Gapmer as in the uniform wings thioate |
| 12 | 5'-TsCsCs <u>GsTsCs AsTsCs Gs CsTs</u> CsCsTs CsAsGs GsG-3' | P=S | 2'-MOE | Gapmer in the with wings MOE as control |
| 13 | 5'-TsCsAs<u>GsTsAs AsTsAsGsCs CsGsCsCsCsAsCsAsTs</u> GsC-3' | P=S | 2'-MOE | Gapmer in the with wings MOE as control | underlined portions of sequences are 2'-deoxy

Procedure 4
General Procedure for the Evaluation of 2'-O-DMAEOE Oligomeric Compounds Targeted to HCV Uniformly modified 2'-O-DMAEOE phosphodiester oligomeric compounds are evaluated for antisense inhibition of HCV gene via a translation arrest mechanism.

Hepatitis C virus (HCV) is known to be responsible for liver disease in many millions of people throughout the world. HCV is an enveloped, positive-strand RNA virus of the flavivirus family. Initial infections in humans are typically asymptomatic, but chronic infection often ensues in which liver cirrhosis and hepatocellular carcinoma are long-term sequelae. Interferon-α (IFN-α) therapy is widely used in attempts to eradicate the virus from chronically infected individuals, but long-term remissions are achieved in only about 20% of patients, even after 6 months of therapy. So far, there is no antiviral drug available for the treatment of HCV. (Blair et al., 1998). Drug discovery and development efforts have been hampered by the lack of suitable cell culture replication assays for HCV, and vaccine production has been hampered by genetic variability of the virus' envelope genes. Specific inhibitors of cloned viral enzymes such as proteases and the viral polymerase have not yet been reported.

Antisense oligonucleotide therapy represents a novel approach to the control of HCV infection. Several antisense oligomeric compounds complementary to HCV RNA sequences adjacent to the polyprotein initiation codon of HCV have been designed at Isis (Hanecak et al., *J. Virol.*, 1996, 70, 5203–5212). The target genome is highly conserved among independent HCV isolates.

It was shown that an RNase H-independent antisense oligonucleotide had greater activity than its parent phosphorothioate (which will work by RNase H mechanism) which was targeted to the AUG site of a core protein sequence of HCV in a human hepatocyte cell line employing a uniformly modified 2'-O-(methoxyethyl) phosphodiester (P=O 20 mer) (Hanecak et al., *J. Virol.*, 1996, 70, 5203–5212). Hepatitis C virus core protein levels were reduced as efficiently as the corresponding 2'-deoxyphosphorothioate with an $IC_{50}$ of 100 nm. SEQ ID NO: 15 was a potent inhibitor of core protein expression without affecting HCV RNA levels. This suggested the inhibition of HCV translation. The parent compound (SEQ ID NO: 14) had Tm of 50.8° C. while the 2'-MOE compound (SEQ ID NO: 15) had a Tm of 83.8° C. Thus, SEQ ID NO: 15 had a better affinity for HCV RNA. The replicative cycle of HCV takes place in the cytoplasm of infected cells, in which RNase H levels have been reported to reduce relative to those of the nucleus. For this reason, it is better to utilize an antisense oligonucleotide which will work by non-RNase H mechanism to inhibit HCV. Oligonucleotide SEQ ID NO: 15 is an attractive lead since it contains a P=O linkage with a 21'-MOE modification. SEQ ID NO: 16 will be tested in accordance with the testing of SEQ ID NO: 14 and 15.

TABLE 4

5'-TTT AGG ATT CGT GCT CAT GG-3'
Antisense Oligonucleotide Targeting HCVC 5'-NCR
Nucleotide Numbers 340–359

| SEQ ID NO: | Backbone | 2'-modification | Tm (° C.) |
|---|---|---|---|
| 14 | P=S | 2'-deoxy | 50.8 |
| 15 | P=O | 2'-MOE | 83.8 |
| 16 | P=O | 2'-2'-O-DMAEOE | |

Procedure 5
In vitro Assays

Isis antisense oligomeric compounds complementary to the HCV polyprotein initiation codon sequence are known to inhibit expression of the viral core protein in immortalized cell lines engineered to express HCV RNA from recombinant DNA integrated into the host cell genome (Hanecak ibid). Non-complementary control oligomeric compounds have no effect on HCV RNA or protein levels in this system. H8Ad17C cells will be treated with a range of concentration of oligomeric compounds shown in Table 4 above, especially SEQ ID NO: 16, (0–200 nm) in the presence of cationic lipids and total protein levels will be evaluated 20 hours later by western blot analysis.

Procedure 6
In vivo Model for HCV

Animal models of HCV infection are not readily available. An alternative approach has been developed to evaluate antisense oligomeric compounds to inhibit HCV gene expression in livers of mice. For these experiments, HCV sequences, including SEQ ID NO: 15 target sequence, were fused to a luciferase reporter gene and inserted into a Vaccinia virus. Infection of mice with this recombinant vaccination virus results in quantifiable levels of luciferase in liver tissue. Potent phosphorothioate antisense oligomeric compounds have been shown to work in this model. SEQ ID NO: 16 (the 2'-O-DMAEOE RNA analog of SEQ ID NO: 15) will be evaluated for inhibition of expression of the HCV-luciferase construct in livers of mice infected with the recombinant vaccinia virus. Inhibition will be evaluated for sequence-dependency and dose response. HCV-luciferase expression in livers of mice infected with a control vaccinia virus vector lacking HCV target sequences will be used as control and the effect of antisense drug in these control systems will be evaluated. (Antisense oligonucleotide-mediated inhibition of hepatitis C virus gene expression in mouse liver (Anderson et al., Meeting Abstracts, International Hepatitis Meeting, Hawaii, 1997).

Procedure 7
In vivo Nuclease Resistance

The in vivo Nuclease Resistance of gapmers having the 2'-O-DMAEOE is studied in mouse plasma and tissues (kidney and liver). For this purpose, the C-raf oligonucleotide series SEQ ID NO: 17 will be used and the following five oligomeric compounds listed in Table 5 below will be evaluated for their relative nuclease resistance.

TABLE 5

| SEQ ID NO: | Sequence | Backbone | Description |
|---|---|---|---|
| 17 | 5'-ATG CAT TCT GCC CCA AGGA-3' | P=S, 2'-H | (control) rodent C-raf antisense oligo |
| 18 | AoToGoCoAsTsTsCsTsGs CsCsCsCsAoAoGoGoA | P=O/P=S/ P=O | (control) 2'-MOE/2'-H/ 2'-MOE |
| 19 | AsTsGsCsAsTsTsCsTsGs CsCsCsCsAsAsGsGsA | P=S | (control) 2'-MOE/2'-H/2'-MOE |
| 20 | AoToGoCoAsTsTsCsTsGs CsCsCsCsAoAoGoGoA | P=O/P=S/ P=O | 2'-2'-O-DMAEOE/ 2'-H/2'-2'-O-DMAEOE |
| 21 | AsTsGsCsAsTsTsCsTsGs CsCsCsCsAsAsGsGsA | P=S | 2'-2'-O-DMAEOE/ 2'-H/2'-2'-O-DMAEOE |

Procedure 8

Animal Studies

For each oligonucleotide to be studied, 9 male BALB/c mice (Charles River, Wilmington, Mass.), weighing about 25 g are used (Crooke et al., *J. Pharmacol. Exp. Ther.,* 1996, 277, 923). Following a 1-week acclimation, the mice receive a single tail vein injection of oligonucleotide (5 mg/kg) administered in phosphate buffered saline (PBS), pH 7.0. The final concentration of oligonucleotide in the dosing solution is (5 mg/kg) for the PBS formulations. One retro-orbital bleed (either 0.25, 9.05, 2 or 4 post dose) and a terminal bleed (either 1, 3, 8 or 24 h post dose) is collected from each group. The terminal bleed (approximately 0.6–0.8 mL) is collected by cardiac puncture following ketamine/xylazine anesthesia. The blood is transferred to an EDTA-coated collection tube and centrifuged to obtain plasma. At termination, the liver and kidneys will be collected from each mouse. Plasma and tissues homogenates will be used for analysis for determination of intact oligonucleotide content by CGE. All samples will be immediately frozen on dry ice after collection and stored at −80° C. until analysis.

Procedure 9

The binding affinity as measured by Tm was evaluated for oligomeric compounds having the 2'-O-[2-(2-N,N-dimethylaminoethyl)oxyethyl] modification. 5-methyl-2'-O-[2-(2-N,N-dimethylaminoethyl)oxyethyl] (modified T) was incorporated at selected positions in oligonucloetides and binding was measured to complementary RNA oligomeric compounds.

TABLE 6

| SEQ ID NO: | Sequence | Backbone | Mass Calculated | Mass Observed |
|---|---|---|---|---|
| 22 | TCC AGG TGT CCG CAT C | PO | 5660.3[a] | 5659.1[a] |
| 23 | CTC GTA CTT TTC CGG TCC | PO | 5912.2 | 5913.5 |
| 24 | GCG TTT TTT TTT TGC G | PO | 6487.3[a] | 6488.5[a] |
| 25 | GAT CT | PO | 1910.6[a] | 1910.8[a] |
| 26 | TTT TTT TTT TTT TTT T | PO | 6544.7[a] | 6542.62[a] |

[a]as DMT-on, underlined nucleosides are 2'-O-[2-(2-N,N-dimethylaminoethyl)oxyethyl]-5-methyl uridine (2'-sub-T)

TABLE 7

| | | Tm values | | | |
|---|---|---|---|---|---|
| SEQ ID NO: Sequence | Target DNA Tm | ΔTm | ΔTm/ mod. | Target RNA Tm | ΔTm | ΔTm/ mod. |
| 27 TCC AGG TGT CCG CAT C | not determined | | | 62.3 | | |
| 22 TCC AGG TGT CCG CAT C | not determined | | | 65.6 | 3.3 | 0.83° |
| 28 GCG TTT TTT TTT TGC G | 54.2 | | | 48.1 | | |
| 24 GCG TTT TTT TTT TGC G | 50.0 | −4.1 | −4.1 | 59.7 | 10.6 | 1.1° |

Underlined nucleosides are 2'-O-[2-(2-N,N-dimethylaminoethyl)oxyethyl] modified.

The 2'-O-[2-(2-N,N-dimethylaminoethyl)oxyethyl] modified nucleosidic monomers show increased Tm as compared to unmodified DNA as shown in Table 7.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An oligomeric compound having at least one nucleoside of the formula:

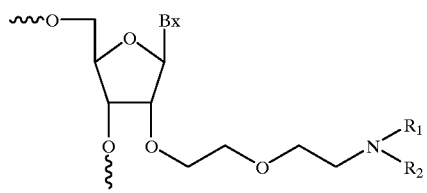

wherein

Bx is a heterocyclic base;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid, amide or an ester;

or $R_1$ and $R_2$, together, are a nitrogen protecting group or are joined in a ring structure that optionally includes an additional heteroatom selected from N and O; and each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O.

2. The oligomeric compound of claim 1 wherein $R_1$ is H, $C_1$–$C_{10}$ alkyl or $C_1$–$C_{10}$ substituted alkyl and $R_2$ is $C_1$–$C_{10}$ substituted alkyl.

3. The oligomeric compound of claim 2 wherein $R_1$ is $C_1$–$C_{10}$ alkyl.

4. The oligomeric compound of claim 2 wherein $R_2$ is $C_1$–$C_{10}$ substituted alkyl and the substituent is $NH_3^+$ or $N(R_3)(R_4)$.

5. The oligomeric compound of claim 2 wherein $R_1$ and $R_2$ are both $C_1$–$C_{10}$ substituted alkyl.

6. The oligomeric compound of claim 5 wherein said substituents are, independently, $NH_3^+$ or $N(R_3)(R_4)$.

7. The oligomeric compound of claim 1 wherein $R_1$ and $R_2$ are each $C_1$–$C_{10}$ alkyl.

8. The oligomeric compound of claim 1 wherein $R_1$ and $R_2$ are joined in a ring structure that can include at least one heteroatom selected from N and O.

9. The oligomeric compound of claim 8 wherein said ring structure is imidazole, piperidine, morpholine or a substituted piperazine.

10. The oligomeric compound of claim 9 wherein the substituent on said piperazine is $C_1$–$C_{12}$ alkyl.

11. The oligomeric compound of claim 1 wherein said heterocyclic base is a purine or a pyrimidine.

12. The oligomeric compound of claim 11 wherein said heterocyclic base is adenine, cytosine, 5-methylcytosine, thymine, uracil, guanine or 2-aminoadenine.

13. The oligomeric compound of claim 1 comprising from about 5 to about 50 nucleosides.

14. The oligomeric compound of claim 1 comprising from bout 8 to about 30 nucleosides.

15. The oligomeric compound of claim 1 comprising from about 15 to about 25 nucleosides.

16. A compound of the formula:

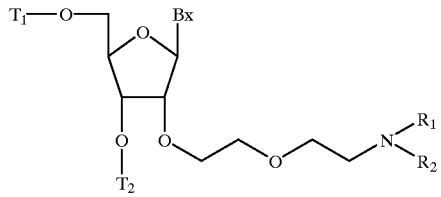

wherein:

Bx is a heterocyclic base;

$T_1$ and $T_2$, independently, are OH, a protected hydroxyl, an activated phosphorus group, a reactive group for forming an internucleotide linkage, a nucleoside, a nucleotide, an oligonucleoside an oligonucleotide or a linkage to a solid support;

each $R_1$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid, amide or an ester;

or $R_1$ and $R_2$, together, are a nitrogen protecting group or are joined in a ring structure that optionally includes an additional heteroatom selected from N and O; and each $R_3$ and $R_4$ is, independently, H, $C_1$–$C_{10}$ alkyl, a nitrogen protecting group, or $R_3$ and $R_4$, together, are a nitrogen protecting group;

or $R_3$ and $R_4$ are joined in a ring structure that optionally includes an additional heteroatom selected from N and O.

17. The compound of claim 16 wherein $R_1$ is H, $C_1$–$C_{10}$ alkyl or $C_1$–$C_{10}$ substituted alkyl and $R_2$ is $C_1$–$C_{10}$ substituted alkyl.

18. The compound of claim 17 wherein $R_1$ is $C_1$–$C_{10}$ alkyl.

19. The compound of claim 17 wherein $R_2$ is $C_1$–$C_{10}$ substituted alkyl and the substituent is $NH_3^+$ or $N(R_3)(R_4)$.

20. The compound of claim 17 wherein $R_1$ and $R_2$ are both $C_1$–$C_{10}$ substituted alkyl.

21. The compound of claim 20 wherein said substituents are, independently, $NH_3^+$ or $N(R_3)(R_4)$.

22. The compound of claim 16 wherein $R_1$ and $R_2$ are each $C_1$–$C_{10}$ alkyl.

23. The compound of claim 16 wherein $R_1$ and $R_2$ are joined in a ring structure that can include at least one heteroatom selected from N and O.

24. The compound of claim 23 wherein said ring structure is imidazole, piperidine, morpholine or a substituted piperazine.

25. The compound of claim 24 wherein said substituted piperazine is substituted with a $C_1$–$C_{12}$ alkyl.

26. The compound of claim 25 wherein said heterocyclic base is a purine or a pyrimidine.

27. The compound of claim 26 wherein said heterocyclic base is adenine, cytosine, 5-methylcytosine, thymine, uracil, guanine or 2-aminoadenine.

28. The compound of claim 16 wherein $T_1$ is a hydroxyl protecting group.

29. The compound of claim 16 wherein $T_2$ is an activated phosphorus group or a connection to a solid support.

30. The compound of claim 29 wherein said solid support material is microparticles.

31. The compound of claim 29 wherein said solid support material is CPG.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

```
<220> FEATURE:
<221> NAME/KEY: misc_feature
<222> LOCATION: (1)..(20)
<223> OTHER INFORMATION: 2'-O-[2-(2-N,N-dimethylaminoethyl)oxyethyl]-5-
      methyl; phosphorothioate linkage
<220> FEATURE:
<221> NAME/KEY: misc_feature
<222> LOCATION: (2)..(2)
<223> OTHER INFORMATION: 5-methyl-C
<220> FEATURE:
<221> NAME/KEY: misc_feature
<222> LOCATION: (10)..(10)
<223> OTHER INFORMATION: 5-methyl-C
<220> FEATURE:
<221> NAME/KEY: misc_feature
<222> LOCATION: (18)..(18)
<223> OTHER INFORMATION: 5-methyl-C

<400> SEQUENCE: 1
tctgagtagc agaggagctc                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: 2'-O-[2-N,N-dimethylaminoethyl)oxyethyl]-5-
      methyl; phosphodiester linkage
<220> FEATURE:
<221> NAME/KEY: misc_feature
<222> LOCATION: (2)..(2)
<223> OTHER INFORMATION: 5-Methyl-C
<220> FEATURE:
<221> NAME/KEY: misc_feature
<222> LOCATION: (10)..(10)
<223> OTHER INFORMATION: 5-Methyl-C
<220> FEATURE:
<221> NAME/KEY: misc_feature
<222> LOCATION: (18)..(18)
<223> OTHER INFORMATION: 5-Methyl-C

<400> SEQUENCE: 2
tctgagtagc agaggagctc                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: 2'-O-[2-N,N-dimethylaminoethyl)oxyethyl]-5-
      methyl; phosphorothioate linkage
<220> FEATURE:
<221> NAME/KEY: misc_feature
<222> LOCATION: (4)..(4)
<223> OTHER INFORMATION: 5-Methyl-C
<220> FEATURE:
<221> NAME/KEY: misc_feature
<222> LOCATION: (7)..(14)
<223> OTHER INFORMATION: phosphorothioate linkage
<220> FEATURE:
<221> NAME/KEY: misc_feature
<222> LOCATION: (8)..(8)
<223> OTHER INFORMATION: 5-Methyl-C
<220> FEATURE:
<221> NAME/KEY: misc_feature
<222> LOCATION: (11)..(15)
<223> OTHER INFORMATION: 5-Methyl-C
```

```
<220> FEATURE:
<221> NAME/KEY: misc_feature
<222> LOCATION: (15)..(20)
<223> OTHER INFORMATION: 2'-O-[2-(2-N,N-dimethylaminoethyl)oxyethyl]-5-
      methyl; phosphorothioate linkage

<400> SEQUENCE: 3
atgcattctg cccccaagga                                                      20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (2)..(4)
<223> OTHER INFORMATION: 5-Methyl-C
<220> FEATURE:
<221> NAME/KEY: misc_feature
<222> LOCATION: (8)..(8)
<223> OTHER INFORMATION: 5-Methyl-C
<220> FEATURE:
<221> NAME/KEY: misc_feature
<222> LOCATION: (12)..(12)
<223> OTHER INFORMATION: 5-Methyl-C
<220> FEATURE:
<221> NAME/KEY: misc_feature
<222> LOCATION: (13)..(20)
<223> OTHER INFORMATION: 2'-O-[2-(2-N,N-dimethylaminoethyl)oxyethyl]-5-
      methyl
<220> FEATURE:
<221> NAME/KEY: misc_feature
<222> LOCATION: (15)..(16)
<223> OTHER INFORMATION: 5-Methyl-C
<220> FEATURE:
<221> NAME/KEY: misc_feature
<222> LOCATION: (19)..(19)
<223> OTHER INFORMATION: 5-Methyl-C

<400> SEQUENCE: 4
gcccaagctg gcatccgtca                                                      20

<210> SEQ ID NO 5
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (16)..(19)
<223> OTHER INFORMATION: 2'-modified T

<400> SEQUENCE: 5
tttttttttt tttttttt                                                        19

<210> SEQ ID NO 6
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: phosphorothioate linkage
```

-continued

```
<400> SEQUENCE: 6
tccgtcatcg ctcctcaggg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: phosphorothioate linkage

<400> SEQUENCE: 7
tcagtaatag gcccacatgg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: phosphodiester linkage
<220> FEATURE:
<221> NAME/KEY: misc_feature
<222> LOCATION: (4)..(12)
<223> OTHER INFORMATION: phosphorothioate linkage; 2-deoxy
<220> FEATURE:
<221> NAME/KEY: misc_feature
<222> LOCATION: (13)..(20)
<223> OTHER INFORMATION: phosphodiester linkage

<400> SEQUENCE: 8
ttcgtcatcg ctcctcaggg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (4)..(12)
<223> OTHER INFORMATION: 2'-deoxy

<400> SEQUENCE: 9
tccgtcatcg ctcctcaggg                                              20

<210> SEQ ID NO 10
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: phosphodiester linkage
<220> FEATURE:
<221> NAME/KEY: misc_feature
<222> LOCATION: (4)..(16)
<223> OTHER INFORMATION: phosphorothioate linkage; 2'-deoxy
```

```
<220> FEATURE:
<221> NAME/KEY: misc_feature
<222> LOCATION: (17)..(26)
<223> OTHER INFORMATION: phosphodiester linkage

<400> SEQUENCE: 10
tcagtaatag ccgccgcccc acatgg                                          26

<210> SEQ ID NO 11
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(23)
<223> OTHER INFORMATION: phosphorothioate linkage
<220> FEATURE:
<221> NAME/KEY: misc_feature
<222> LOCATION: (4)..(12)
<223> OTHER INFORMATION: 2'-deoxy

<400> SEQUENCE: 11
tcagtaatag ccgccccaca tgc                                             23

<210> SEQ ID NO 12
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (4)..(12)
<223> OTHER INFORMATION: 2'-deoxy

<400> SEQUENCE: 12
tccgtcatcg ctcctcaggg                                                 20

<210> SEQ ID NO 13
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(21)
<223> OTHER INFORMATION: phosphorothioate linkage
<220> FEATURE:
<221> NAME/KEY: misc_feature
<222> LOCATION: (4)..(12)
<223> OTHER INFORMATION: 2'-deoxy

<400> SEQUENCE: 13
tcagtaatag ccgccccaca tgc                                             23

<210> SEQ ID NO 14
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
```

```
<223> OTHER INFORMATION: phosphorothioate linkage; 2'-deoxy

<400> SEQUENCE: 14
tttaggattc gtgctcatgg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: phosphodiester linkage; 2'-MOE

<400> SEQUENCE: 15
tttaggattc gtgctcatgg                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: 2'2'-O-DMAEOE

<400> SEQUENCE: 16
tttaggattc gtgctcatgg                                              20

<210> SEQ ID NO 17
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(19)
<223> OTHER INFORMATION: phosphorothioate linkage

<400> SEQUENCE: 17
atgcattctg ccccaagga                                               19

<210> SEQ ID NO 18
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: phosphodiester linkage; 2'-MOE
<220> FEATURE:
<221> NAME/KEY: misc_feature
<222> LOCATION: (5)..(5)
<223> OTHER INFORMATION: phosphorothioate linkage; 2'-MOE
<220> FEATURE:
<221> NAME/KEY: misc_feature
<222> LOCATION: (6)..(14)
<223> OTHER INFORMATION: phosphorothioate linkage
<220> FEATURE:
<221> NAME/KEY: misc_feature
<222> LOCATION: (15)..(19)
<223> OTHER INFORMATION: phosphodiester linkage; 2'-MOE

<400> SEQUENCE: 18
```

```
atgcattctg ccccaagga                                              19

<210> SEQ ID NO 19
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(19)
<223> OTHER INFORMATION: phosphorothioate linkage
<220> FEATURE:
<221> NAME/KEY: misc_feature
<222> LOCATION: (1)..(5)
<223> OTHER INFORMATION: 2'-MOE
<220> FEATURE:
<221> NAME/KEY: misc_feature
<222> LOCATION: (15)..(19)
<223> OTHER INFORMATION: 2'-MOE

<400> SEQUENCE: 19
atgcattctg ccccaagga                                              19

<210> SEQ ID NO 20
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: phosphodiester linkage; 2'-2'-O-DMAEOE
<220> FEATURE:
<221> NAME/KEY: misc_feature
<222> LOCATION: (5)..(5)
<223> OTHER INFORMATION: phosphorothioate linkage; 2'-2'-O-DMAEOE
<220> FEATURE:
<221> NAME/KEY: misc_feature
<222> LOCATION: (6)..(14)
<223> OTHER INFORMATION: phosphorothioate linkage
<220> FEATURE:
<221> NAME/KEY: misc_feature
<222> LOCATION: (15)..(19)
<223> OTHER INFORMATION: phosphodiester linkage; 2'-2'-O-DMAEOE

<400> SEQUENCE: 20
atgcattctg ccccaagga                                              19

<210> SEQ ID NO 21
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(19)
<223> OTHER INFORMATION: phosphorothioate linkage
<220> FEATURE:
<221> NAME/KEY: misc_feature
<222> LOCATION: (1)..(5)
<223> OTHER INFORMATION: 2'-2'-O-DMAEOE
<220> FEATURE:
<221> NAME/KEY: misc_feature
<222> LOCATION: (15)..(19)
<223> OTHER INFORMATION: 2'-2'-O-DMAEOE

<400> SEQUENCE: 21
atgcattctg ccccaagga                                              19
```

<210> SEQ ID NO 22
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: 2'-O-[2-(2-N,N-dimethylaminoethyl)oxyethyl]-
      5-methyl uridine (2'-sub-T)
<220> FEATURE:
<221> NAME/KEY: misc_feature
<222> LOCATION: (7)..(7)
<223> OTHER INFORMATION: 2'-O-[2-(2-N,N-dimethylaminoethyl)oxyethyl]-
      5-methyl uridine (2'-sub-T)
<220> FEATURE:
<221> NAME/KEY: misc_feature
<222> LOCATION: (9)..(9)
<223> OTHER INFORMATION: 2'-O-[2-(2-N,N-dimethylaminoethyl)oxyethyl]-
      5-methyl uridine (2'-sub-T)
<220> FEATURE:
<221> NAME/KEY: misc_feature
<222> LOCATION: (15)..(15)
<223> OTHER INFORMATION: 2'-O-[2-(2-N,N-dimethylaminoethyl)oxyethyl]-
      5-methyl uridine (2'-sub-T)

<400> SEQUENCE: 22
tccaggtgtc cgcatc                                                  16

<210> SEQ ID NO 23
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(11)
<223> OTHER INFORMATION: 2'-O-[2-(2-N,N-dimethylaminoethyl)oxyethyl]-
      5-methyl uridine (2'-sub-T)

<400> SEQUENCE: 23
ctcgtacttt tccggtcc                                                18

<210> SEQ ID NO 24
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(13)
<223> OTHER INFORMATION: 2'-O-[2-(2-N,N-dimethylaminoethyl)oxyethyl]-
      5-methyl uridine (2'-sub-T)

<400> SEQUENCE: 24
gcgttttttt tttgcg                                                  16

<210> SEQ ID NO 25
<211> LENGTH: 5
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: 2'-O-[2-(2-N,N-dimethylaminoethyl)oxyethyl]-
      5-methyl uridine (2'-sub-T)

```
-continued

<400> SEQUENCE: 25 gatct                                                              5

<210> SEQ ID NO 26
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (16)..(19)
<223> OTHER INFORMATION: 2'-O-[2-(2-N,N-dimethylaminoethyl)oxyethyl]-
      5-methyl uridine (2'-sub-T)

<400> SEQUENCE: 26
tttttttttt ttttttttt                                              19

<210> SEQ ID NO 27
<211> LENGTH: 16
<212> TYPE: DNA
<213> ORGANISM: Artificial Sequence
<220> FEATURE:
<223> OTHER INFORMATION: Synthetic construct

<400> SEQUENCE: 27
tccaggtgtc cgcatc                                                 16

<210> SEQ ID NO 26
<211> LENGTH: 19
<212> TYPE: DNA
<213> ORGANISM: Artificial Sequence
<220> FEATURE:
<223> OTHER INFORMATION: Synthetic construct
<210> SEQ ID NO 28
<211> LENGTH: 16
<212> TYPE: DNA
<213> ORGANISM: Artificial Sequence
<220> FEATURE:
<223> OTHER INFORMATION: Synthetic construct

<400> SEQUENCE: 28
gcgttttttt tttgcg                                                 16
```